United States Patent [19]

Gracovetsky

[11] Patent Number: 4,971,069

[45] Date of Patent: Nov. 20, 1990

[54] METHOD AND EQUIPMENT FOR EVALUATING THE FLEXIBILITY OF A HUMAN SPINE

[75] Inventor: Serge Gracovetsky, St Lambert, Canada

[73] Assignee: Diagnospine Research Inc., Montréal, Canada

[21] Appl. No.: 250,215

[22] Filed: Sep. 28, 1988

[30] Foreign Application Priority Data

Oct. 5, 1987 [CA] Canada .................................. 548627

[51] Int. Cl.$^5$ .................................................. A61B 5/11
[52] U.S. Cl. ....................................... 128/781; 128/733
[58] Field of Search ....................... 128/781, 782, 733; 33/511, 512

[56] References Cited

U.S. PATENT DOCUMENTS

| | | |
|---|---|---|
| 4,600,012 | 7/1986 | Kohayakawa et al. |
| 4,655,227 | 4/1987 | Gracovetsky. |
| 4,664,130 | 5/1987 | Gracovetsky. |
| 4,699,156 | 10/1987 | Gracovetsky. |
| 4,832,049 | 5/1989 | Matsushita et al. ................ 33/512 |

FOREIGN PATENT DOCUMENTS

245098A 11/1987 European Pat. Off. ............ 128/781

OTHER PUBLICATIONS

Theusohn et al., Biomedizinische Technik, Dec. 1980, pp. 324–330.
Lido-Tech Report, Mar. 1987, vol. 1, No. 1, published by Loredan Biomedical.

*Primary Examiner*—Kyle L. Howell
*Assistant Examiner*—John C. Hanley
*Attorney, Agent, or Firm*—Robic

[57] ABSTRACT

A non-invasive method and equipment for the evaluation of the flexibility of the spine of a patient and identification of possible mechanical injuries in the lumbar portion of this spine. A string of skin-markers is fixed onto the skin of the back of the patient in the midline of his spine from at least cervical vertebra $C_7$ down to at least sacral vertebra $S_3$. Two other skin-markers are fixed onto the skin of the back of the patient in a bilateral and symmetrical manner on the crests of his ilium. The relative positions of all the skin-markers are then monitored and recorded as he flexes forward in this sagittal plane and the so recorded positions are processed to determine the ranges of hip and spine motions in the sagittal plane, which can be compared with each other and with results obtained from a group of "normal" patients to determine any discrepancy or singularity in the flexibility of the spine. The data obtained may be correlated with other data obtainable by the same equipment to provide a full 3D dynamic motion analysis of trunk, spine, pelvis and inter-segmental movement.

18 Claims, 20 Drawing Sheets

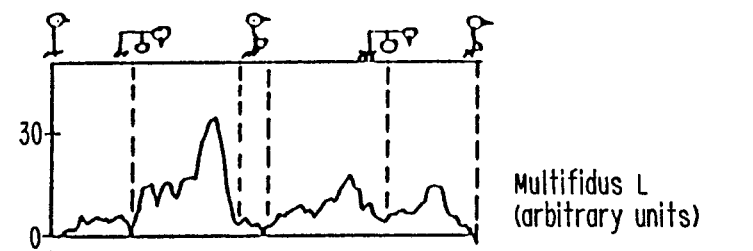
FIG. 4A
Multifidus L (arbitrary units)
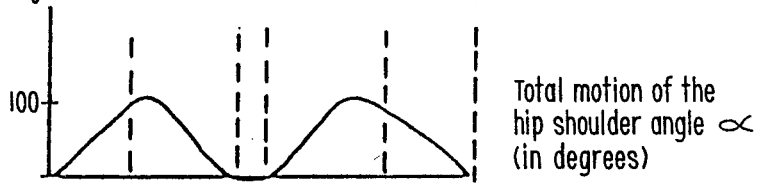
FIG. 4B
Total motion of the hip shoulder angle $\alpha$ (in degrees)
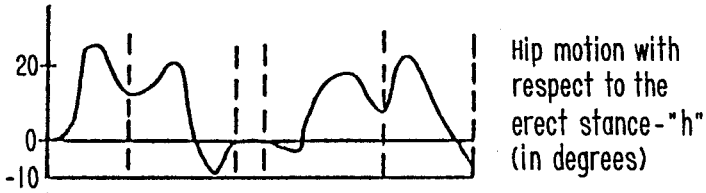
FIG. 4C
Hip motion with respect to the erect stance-"h" (in degrees)
FIG. 4D
Gross range of motion of spine-"s" D-B-C (in degrees)
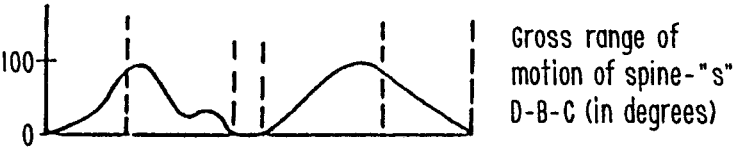
FIG. 4E
Lumbosacral angle $\gamma$ calculated from the markers position
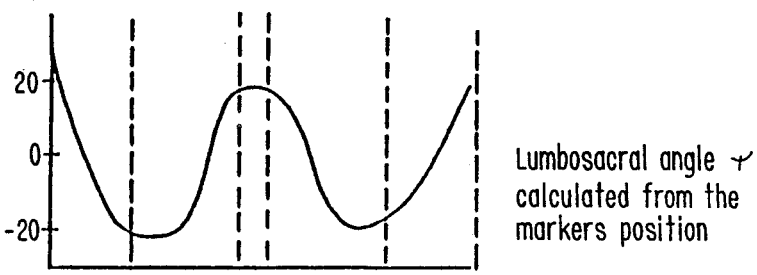
FIG. 4F
Percentage elongation of the arc sustained by the markers — the reference is the erect stance
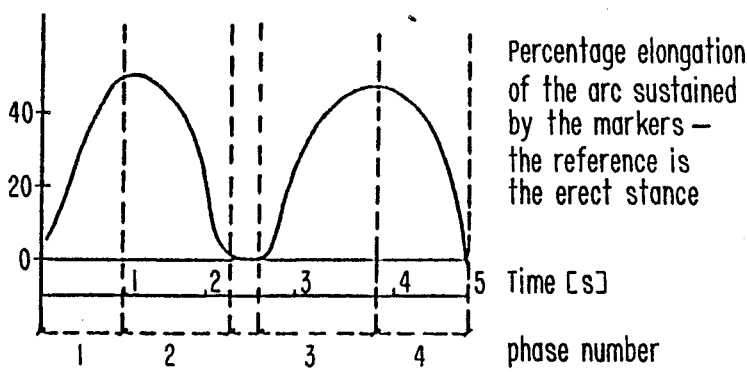

motion of the hip in the sagittal plane contribution of the spine to the total motion lumbosacral angle $\gamma$ deducted from the position of the markers

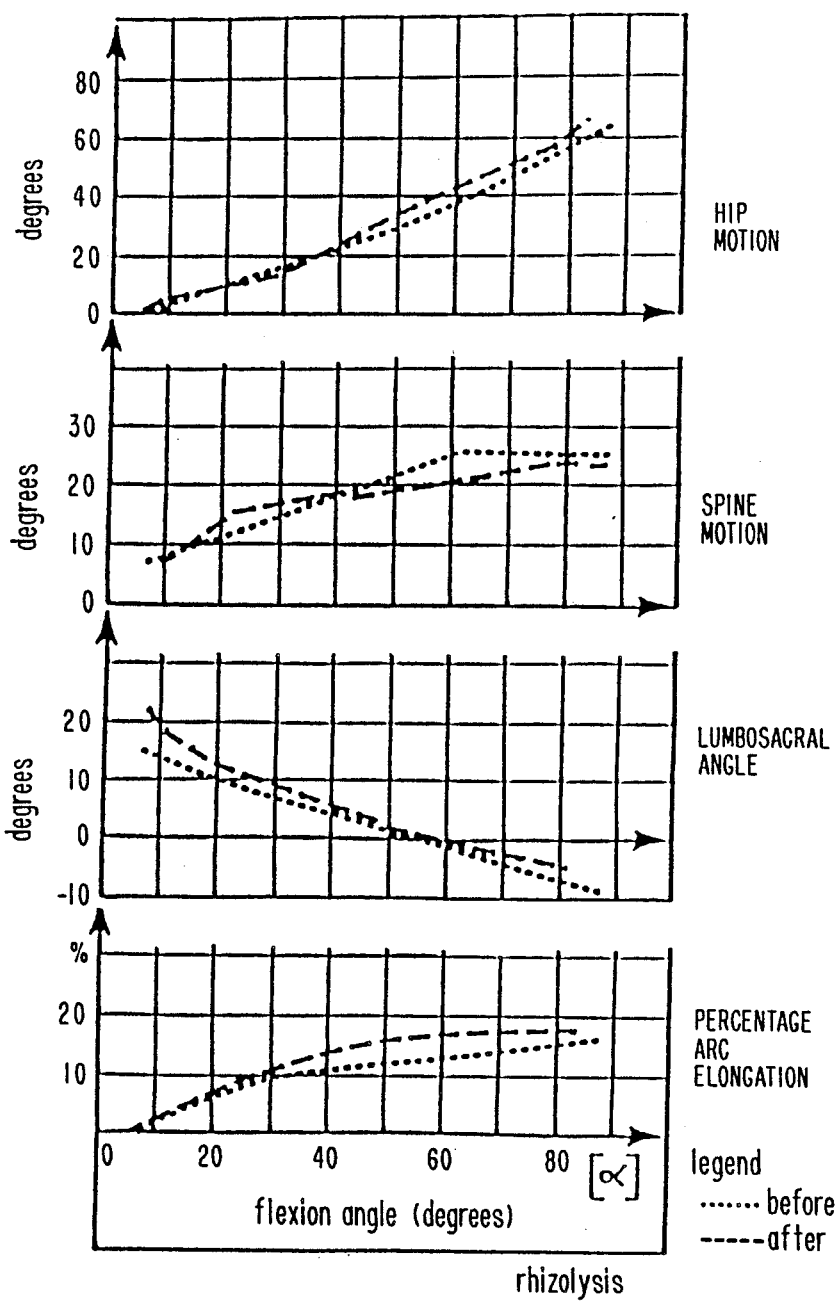
FIG. 9A — HIP MOTION
FIG. 9B — SPINE MOTION
FIG. 9C — LUMBOSACRAL ANGLE
FIG. 9D — PERCENTAGE ARC ELONGATION
flexion angle (degrees) [α]
legend
...... before
----- after
rhizolysis

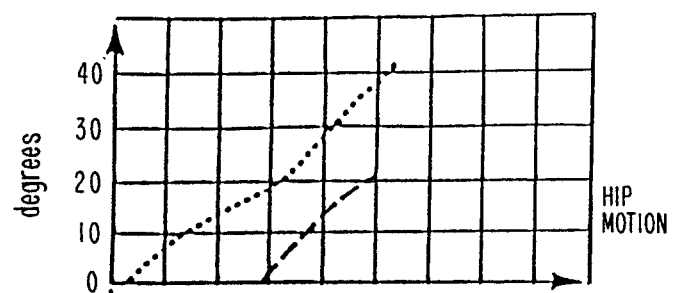
FIG. 11A — HIP MOTION
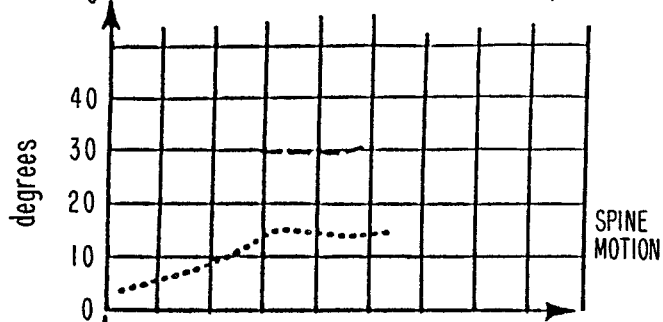
FIG. 11B — SPINE MOTION
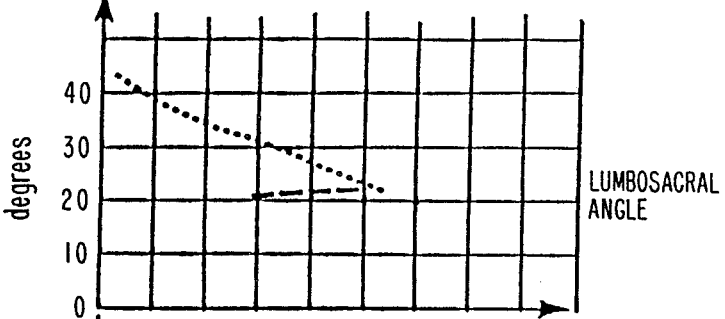
FIG. 11C — LUMBOSACRAL ANGLE
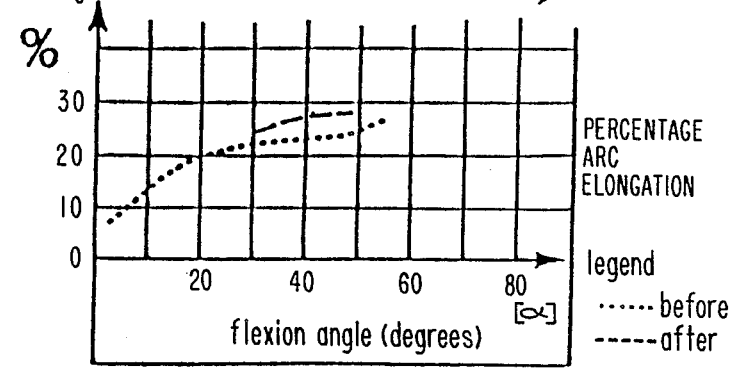
FIG. 11D — PERCENTAGE ARC ELONGATION
legend
······ before
----- after

HIP MOTION

SPINE MOTION

LUMBOSACRAL ANGLE

PERCENTAGE ARC ELONGATION

METHOD AND EQUIPMENT FOR EVALUATING THE FLEXIBILITY OF A HUMAN SPINE

BACKGROUND OF THE INVENTION (a) Field of the invention

The present invention relates to a non-invasive method for a full three-dimensional dynamic free motion analysis of the trunk, spine, pelvis and intersegmental movement of a patient.

More particularly, the invention relates to a non-invasive method for the dynamic evaluation of the flexibility of the spine of a patient and, as a result of this evaluation, the detection and identification of possible mechanical injuries in some portion of this spine, especially the lumbar portion thereof.

The invention also relates to an equipment for carrying out this method.

(b) Brief description of the prior art

It is well known in the medical art that common back disorders have a mechanical etiology. It is also well known from pathological studies that there are two common patterns of disc injury which correspond to two different types of mechanical failure of the spine.

The first type of common injury hereinafter referred to as "compression injury", usually starts by a central damage to the disk with fracture o varying magnitude of the end plates of the adjacent vertebrae, sometimes followed by injection of part of the nucleus into the vertebral body. In this particular case, the injured end plate permits the invasion of the avascular nucleus and of the avascular inner portion of the annulus by granulation tissue ingrowing through the fractured end plate, such an invasion leading to gradual destruction of the avascular nucleus and inner annulus. In the early stages, the facet joints of the vertebrae are not affected and the outer annulus survives while the center portion of the disc is destroyed. With progression, the disc loses its thickness while the outer layer of the annulus remains relatively well preserved. With lost of disk thickness, the facet joint subluxates and develops a moderate degree of osteoarthritis.

Usually, the fracture of the end plate of a vertebra is an undisplaced fracture of cancellous bone which heals rapidly. The symptoms are short lived, typically lasting two weeks. The facet joint arthritis appears late. At this stage, symptoms may also arise from the reduction in size of the spinal canal (lateral or central spinal stenosis).

The other type of common injury hereinafter referred to as "torsional injury", is characterized by a damage to the annulus occurring simultaneously with a damage to the facet joints. The annulus is avulsed from the end plate and its laminae become separated while the central disk and the end plate remain intact. At the later stage, the annulus develops radial fissures while the nucleus remains relatively untouched. The changes in the facet joints are severed with massive joint destruction and osteophytosis similar to hypertropic arthritis. Relatively late in the process, there may be changes in the end-plates and central disks, with consequent collapse of the articular surfaces and chronic synovitis.

In this particular case, the basis injury is to collageneous ligamentous tissue which requires six weeks to regain 60% of its strength. Because the injury involves both the disk and facet joints, it is more difficult for the joint to stabilize itself and recurrence is frequent. The condition is progressive and may lead to spinal stenosis, instability and degenerative spondilolisthesis.

Tests conducted in laboratory have shown that a compression injury is easily produced by compressing a joint between 2 Mpa to 6 Mpa. A torsional injury can be seen with as little as 2 to 3 degrees of forced rotation requiring only 22 to 33 Newton-meters of torque.

Statistically, in a group of patients suffering from back disorders, 64% exhibit torsional injuries whereas 35% exhibit axial compression injuries. Statistics have also shown that torsional injury occurs mainly at the $L_4$-$L_5$ level (almost 76% of forth joint problems are of torsional nature). Statistics have also shown that almost 98% of the compression injuries occur at the $L_5$-$S_1$ level. Statistics have further shown that double injuries where the joint is injured both in compression and torsion, occur in 22% of the cases, invariably at the $L_5$-$S_1$ level.

The following Table I reflects the probabilities of injuries among patients complaining from backache and sciatica, or sciatica alone. As can be seen from this Table, the important frequency of torsional injury cannot be overlooked. As can also be seen, the probability of a third type of injury giving symptoms is very remote.

TABLE I
CLINICAL DETERMINATION OF THE VARIOUS PROBABILITIES OF INJURIES

| JOINT | P (injury) | P (compression) | P (torsion) |
|---|---|---|---|
| $L_5/S_1$ | 47% | 98% | 22% |
| $L_4/L_5$ | 47% | 1%< | 76% |
| $L_3/L_4$ | 5%< | 1%< | 1%< |
| $L_2/L_3$ | 1%< | 1%< | 1%< |
| $L_1/L_2$ | 1%< | 1%< | 1%< |
|  | 100% | 100% | 100% |

It is also well known that health professionals are trained to use symptoms in the determination of diagnoses, the large numbers of known symptoms being quite naturally associated with a large number injuries and diagnoses. Unfortunately, as can be understood from the above short description of the pathology in the case of back disorders, both the compression and torsion injuries may give rise to identical symptomology. Hence, symptoms cannot be used to diagnose a type of injury because identical symptoms may arise from different injuries.

It is also well known in the art that low back pain is the leading cause of disability in North America today, affecting from 8 to 9 million people. It is the most common disability in persons under the age of 45 and the third only after arthritis and heart disease in those over have a low back pain at some time of their lives, usually between the ages of 20 and 50. The fact that problems are so common in people of working age is not coincidental. Indeed, most of the back problems are work-related. As the injury caused by a certain task cannot be identified from the patient's symptoms, it is of course not possible to relate directly a given task to an injury mode, although such a relationship is central to the definition of tasks that will not injure a specific worker.

The economic effects of back pain and injuries are staggering. Back problems are second only to the common cold as a cause of absenteeism in the industry. It is moreover responsible for 93 million lost workdays every year and is a leading cause of reduced work capacity. Hence, an incentive for prevention of back injury is very large.

In order to unequivocally relate a given task to a given injury in the absence of any measurement of the effect of the task on a given joint, it has already been suggested to use mathematical and/or biomechanical models of spine, like the one suggested by J.M. Morris et al in their article "The Role of trunk in stability of the spine", J. Bone and Joint Surg., 43A, 1961. However, a major problem with the known models of spine, including the widely used model of J.M. Morris et al, is that they do not truly reflect the physiological behavior of the spine over the full range of capacity.

Thus, by way of example, the model of J.M. Morris et al assumes, as fundamental hypothesis, that the moment generated by the body weight and any external load carried by the patient is balanced by the combined action of the erectores spinae and the intra-abdominal pressure. This is a very poor representation of physiological behavior which is not supported by observations. Indeed, such a model predicts a total failure of the mechanism at about one fourth of the known potential of a spinal healthy spine.

The major reason why all of the models known to the inventor are defective is essentially because they give an incomplete representation of the actual anatomy of a human being. It is true that a moment-supporting member is required in such a model but this cannot be the abdominal pressure only, as suggested by J.M. Morris et al.

This established fact combined with different other anatomical observations reported in the literature, has led the inventor to devise a new mathematical representation of the anatomy of the human spine including (1) the posterior ligamentous system which has indeed the strength to support any moment generated onto the spine by the body weight and any external load carried by the patient, and (2) the extensors of the hip which have the bulk and the lever arm necessary to supply all the moment requirements to flex the spine.

In greater details, the inventor has been noted that, under normal circumstance, the motion of an individual flexing forward from zero upright down to full flexion is due to a combination of pelvis rotation and spine motion.

In the range of 0° to about 45° (for an unloaded spine), the posterior midline ligament system is generally inactive and, in its place, the erectores spinae and/or the abdominal muscles support most of the moment due to the body weight. From about 45° to full flexion, this moment can be also supported by the midline ligament system without muscular activity. This relaxation phenomenon from muscular to ligamentous support was already noted in the art by W. F. Floyd et al in their article "The Function of the Erector Spinae Muscles in certain Movements and Postures in Man", J. Physiology, volume 129, pp. 184–203, 1955.

Using electromyographis (EMG) measurements, W. F. Floyd et al clearly saw a relation between the moment to be supported and the angle of forward flexion, and realized the meticulous coordination of muscle, ligament and joint movement. They hypothesized that in the case of injury to an intervertebral joint, this delicate coordination will be upset and this would be reflected in change of the E.M.G. pattern. Then, they embarcated on an E.M.G. study and tried to compare statistically the E.M.G. pattern of normal individuals to that of those with common back problems in the performance of a standardized simple weight lifting task. However, they gave up after testing 140 cases because the results were inconsistent.

The mathematical model devised by the inventor, takes it for granted that the pelvis acts as a "supporting base" for the entire spine, and assumes as fundamental hypothesis, that any healthy person will perform a task in such a way as to minimize and equalize the stress at each invertebral joint.

In this model, the main power for a lift is assumed to be generated by the extensors of the hip, such as the Gluteus Maximae.

The moment generated by these muscles is transmitted to the upper extremities by the trunk musculature and the posterior ligamentous system (PLS) which, for the purpose of this discussion, is composed of the midline ligament and the lumbodorsal fascia. Regardless of the inclination of the trunk, the moment generated by the extensors of the hip must equal the sum of the moment generated by the trunk musculature and PLS. Therefore, for any given hip extensor moment, one can find an infinite number of combinations to distribute this moment between trunk muscles and the PLS.

Because of the reserve capacity in performing a small weight lift, a normal individual may select a combination of ligaments and muscles which is not optimum from a stress minimization and equalization point of view. However, the reserve is reduced in the presence of injury. The option of selecting a non-optimum strategy is also reduced.

Assuming that the distribution of moment between ligaments and muscles is controlled by the requirement that stress be minimized and equalized at all lumbar joints, stress at one intervertebral joint will be defined as the ratio of the resultant compressive force acting perpendicular to the bisector of the disk to the area of the disk. In general, when muscles are used, the stress is higher than when either ligament systems are used, because the lever arms of the ligament systems are longer than those of any of the muscles. The midline ligament system can be activated only when the spine is sufficiently flexed. The hip/shoulder angle at which this ligament takes up tension is called $\alpha_o$, which is about 45 degrees for no load. This ligament system is strong enough to support the heaviest lift and hence, when this ligament system is activated, the spinal musculature is no longer required and therefore the muscles are electrically silent. As aforesaid, this is the muscle relaxation phenomenon observed by W. F. Floyd et al.

The thoracodorsal fascia can be activated by the contractions of the abdominal muscles, in particular the internal oblique and T. abdoinis, which exert a pull at its lateral margin only when the abdominal pressure is at sufficient value to maintain a rounded abdominal cavity. This ligament system can therefore be activated for any angle of flexion. This is an essential difference when compared to the midline ligament.

Based on this new mathematical model, the present inventor has devised and patented a new method and equipment for the detection of mechanical injuries in the lumbar spine of the patient and the identification of these injuries.

According to this method which forms the subject matter of Canadian Patent No. 1,220,273 and U.S. Pat. No. 4,655,227 both assigned to DIAGNOSPINE RESEARCH INC., the electromyographic (EMG) activities of the erectores and abdominals of the patient are measured in the bilateral and symmetrical manner with respect to the spine of the patient while the same is flexing forward in the median plane and pulling up a small load. The angle of flexion $\alpha$ of the patient is measured during this flexion and is supplied as variable input to the mathematical model. A computer is used to run the model with its variable input in order to calculate the EMG activities of the erectores and abdominals that would normally be used by a healthy person to produce the same task. The so calculated EMG activities are then compared to the EMG activities actually measured on the patient and the parameters of the models are tuned to fit the calculated EMG activities for those measured on the patient. The amount and type of tuning that are necessary to complete the last step, are sufficient in practice to detect and identify the mechanical injuries that may be present in the lumbar spine of the patient.

Based on the same mathematical model, the present inventor has also devised and patented another method and an equipment for the detection of a mechanical abnormality or injury in the lumbar spine of a patient and for the identification of this abnormality or injury as being of the compression or torsion type.

According to this other method which forms the subject matter of Canadian patent no. 1,220,272 and U.S. Pat. No. 4,664,130 both assigned to DIAGNOSPINE RESEARCH INC., any variation of the lumbar curve of the patient is measured using a combined visual and an electromyographic (EMG) technique, and any discrepancy or asymmetry is detected in said measured variation of lumbar curve. In practice, the absence of any variation or the detection of any discrepancy or asymmetry in the case where a variation is measured, is indicative of the presence of a mechanical abnormality or injury of the lumbar spine of the patient, In greater details, the method forming the subject matter of Canadian patent no. 1,220,272 and its U.S. counterpart U.S. Pat. No. 4,664,130, comprises the following steps.

First of all, a first pair of surface-electrodes is fixed onto the back of the patient in a bilateral and symmetrical manner with respect to his spine in the lumbar zone, in order to record the electromyographic (EMG) activities of erectores of this patient. A second pair of surface-electrodes is fixed in a bilateral manner onto the triangles of Petit of the patient in order to record the EMG activity of his Internal Oblique and a third pair of surface-electrodes is fixed in a bilateral manner behind the thighs of the patient in order to record the EMG activity of his hip extensors.

Then, the muscle activity of the patient is measured with all of the surface-electrodes while he is flexing forward in the median plane and pulling up a small load, and the EMG activities measured by each of the surface electrodes are independently recorded as a function of time. Simultaneously, the angle of flexion $\alpha$ of the patient is measured and recorded as a function of time. This angle $\alpha$ is defined as the dihedral angle between a plane passing through the hips and shoulders of the patient and a vertical plane parallel to the frontal plane of this patient.

Last of all, the recorded EMG activities that are so measured on the patient are processed to calculate the relative variations in activities of the erectores versus the hip extensors (E/H ratio) and of the Internal Oblique versus the hip extensors (A/H ratio) and plotting said E/H and A/H ratios versus $\alpha$, and to calculate the amount of asymmetry "a" between the recorded EMG activities measured on the right side of the patient and the recorded EMG activities measured on the left side of this patient.

The observation of a high A/H ratio which corresponds to an extensive use of the abdominals, with the simultaneous observation of a significant delay in the detection of a sharp variation of the E/H ratio at a given angle $\alpha_o$ or of no variation at all of said E/H ratio when the patient is pulling up the small load, indicate that the patient cannot relax his erectores at the beginning of the lift, such a refusal indicating in turn that the patient has difficulty to flex his spine and therefore has a joint injury of the compression or torsional type.

On the other hand, the observation of a significant variation of "a" when $\alpha$ varies, that is during the lift of the small lead, indicates that the joint injury in the lumbar spine is of the torsional type.

In addition to the above mentioned methods, the present inventor has devised and patented a further method and equipment for the detection of torsional injuries the lumbar spine of the patient, which method and equipment are much simpler than any others.

This method which forms the subject matter of Canadian patent no. 1,219,673 and U.S. Pat. No. 4,699,156 both assigned to DIAGNOSPINE RESEARCH INC., derives from an observation made by the inventor that a healthy spine is characterized by its ability to flex smoothly in any plane. Hence, an injury to any joint of the spine will always result in a reduced flexing range of motion of the spine.

According to this method, a string of separate, dot-sized skin-markers that may consist of small LEDs fired under computer control, are fixed onto the skin of the back of the patient in the midline of his spine from at least thoracic vertebra $T_{10}$ down to at least sacral vertebra $S_3$. A visualization equipment including two cameras spaced apart from each other, is used to observe, monitor and record the relative positions of the skin-markers on the back of the patient as he leans to the left and then to the right off his sagittal plane. The recorded positions of the skin-markers when the patient was leant to the left, are then compared with their recorded positions when the patient was leant to the right in order to determine whether there is a significant difference between both of these recorded positions, and in the case where there is such a significant difference, whether these different recorded positions are symmetrical with respect to the sagittal plane.

In practice, the observation of a non-significant difference between the recorded positions of the skin-markers indicates a refusal by the patient to flex his spine, such a refusal in turn indicating the presence of a double torsional injury having damaged any lumbar intervertebral joints statistically between vertebrae $L_4$ and $L_5$ or $L_5$ and $S_1$. On the other hand, provided that the recorded positions of the skin-markers are different, the observation of a substantial asymmetry between the recorded positions indicates a refusal by the patient to flex his spine in one direction, such a refusal in turn indicating the presence of a simple torsional injury at any lumbar intervertebral joints statistically between vertebrae $L_4$ and $L_5$ or $L_5$ and $S_1$.

The latter method and the very particular equipment used for carrying it out, have been actually reduced into practice and successfully tested. In addition to being a real and true scientific diagnosis tool, this method as well as all the other methods devised by the present inventor and mentioned therein above, have the major advantage of being of the "non-invasive" type, essentially because they do not require "invasive" tools such as X-rays, needles and the like to collect the physiological data necessary for detecting the presence of a mechanical abnormality or injury.

It is worth mentioning that other non-invasive methods are known and presently used for evaluating the musculature involved in truck flexion and extension and/or the flexibility of a patient's back.

By way of example, U.S. Pat. No. 4,600,012 issued on July 15, 1986 to CANON KABUSHIKI KAISHA discloses a method and an apparatus for detecting abnormality in the spine of a patient. According to this method which is based on the presumption that an abnormality in the positions of the shoulders is indicative of an abnormality in the spine, light lines are projected parallel to the spine on the right and left sides of the back of the patient and monitored to determine the positions of the shoulders of this patient while the same is bending forward. The observation of a difference in the heights of the left and right shoulders in the forward bent posture, is allegedly indicative of a spinal abnormality such as a lateral spinal curvature.

The major problem with this method is that there are cases where the shoulder positions may "look" abnormal while the spine is normal and other cases where the shoulder positions look normal but the spine is seriously damaged (by way of example, a compression injury with an end plate fracture will result in the injection of the nucleus in the vertebrae body but will not prevent the patient from getting a symmetrical motion during forward flexion).

French laid-open patent application no. 2,449,433 to Jean MAURER discloses a method and equipment for visualizing spine deformation. According to this method, an adhesive band having a flexibility and elasticity compatible with the body motion in the spinal zone is "glued" onto the skin of the patient's back to follow the axis of his spine. The band supports a helicoidal bellows of flexible material which incorporates a plurality of goniometers for recording and transmitting data indicative of their respective positions and orientations preferably via a cable, to a T.V. monitor. The image displayed on the screen is divided into two parts in which are respectively shown the recorded position of the spine in the sagittal plane of the patient (anteroposterior bends) and the recorded position of the spine in the frontal plane (lateral bends). Reference lines may also be displayed to allow the patient to visualize the difference between a "normal" spine and his spine.

A first problem encountered in the MAUGER's method is that the goniometers used as "sensors" may only give 2-dimensional signals. This is unfortunately a substantial source of error as the coupling motion of a spine is much more complex, 1% of lateral bent of one joint frequently inducing up to 0.66% of simultaneous axial rotation.

Another problem in MAUGER is that the adhesive band used to fix the goniometers must be wide enough to support the bellows and sensors. Because of this width, the band extends on both sides of the epiphysis of each vertebra, along which a very active muscle called multifidus extends. Of course, this muscle "moves" on its own when 10 the spine moves and affects the orientation of the goniometers fixed to the band. Thus, if the patient while he is performing an exercise, has for any reason a muscular spasm, this motion will be sensed by the adjacent goniometer as a spinal motion and will create another very substantial error in the displayed data.

The same problem is obviously encountered in the equipment presently sold by the U.S. Company MOTION ANALYSIS CORPORATION of SANTA ROSA, California, under the trade name SPINE-TRAK. This equipment which is intended to be used for measuring and evaluating "the range of motion of the cervical, thoracic and lumbar spine, the spine kinematics with velocity and acceleration in three movement modes and the total thoraco-lumbar, lumbo-pelvic and femoral-pelvic motion", makes use of strings of skin-markers that are fixed laterally and symmetrically on both sides of the spine, on top of the shoulders and along the hips, or on both sides of the neck, on top of the shoulders and around the skull and whose respective positions are tracked, plotted and processed to evaluate the flexibility of the lumbar or cervical portion of the spine. Once again, most the sensors"(i.e. the skin-markers) used in this equipment, including in particular those used to track the lumbar portion of the spine, are fixed onto muscles that move on their own when the spine moves and thus create errors in the resulting data.

Another equipment is presently offered for sale by the U.S. Company LOREDAN BIOMEDICAL of DAVIS, California, under the trade name LIDO® Back Isokinetic System, to evaluate and rehabilitate the musculature involved in trunk flexion and extension. In this equipment, the patent's pelvis is rigidly strapped and his chest attached to a sliding chest carriage that constrains the trunk to rotate about a single axis. Thus, the patient performs difference isokinetic exercises in either sitting or standing position. During these exercises, the patient's torque and the angular velocity of his movement are measured and used to evaluate his physical condition.

A major limitation of this equipment is that it evaluates the spine function while the patient trunk is allowed to rotate about a single axis while the human spine actually has 24 mobile vertebrae, i.e. 24 centers of rotation, that are also rotate over a moving pelvis.

OBJECTS AND SUMMARY OF THE INVENTION

An object of the present invention is to provide a non-invasive method for the dynamic evaluation of the flexibility of the spine of a patient and, as a result of this evaluation, the detection and identification of possible mechanical injuries in any portion of this spine, which method (1) is as simple as the one disclosed and claimed in Canadian patent No. 1,219,673 and its U.S. counterpart No. 4,699,156;

(2) derives from the same observation that a healthy spine is able to flex smoothly in any plane; and (3) does not have the drawbacks and/or insufficiencies of the known methods briefly disclosed hereinabove.

The method according to the invention however is much broader in scope and application as the one disclosed and claimed in the above patents, in that it is not restricted to the detection of torsional injuries in the lumbar portion of the spine, exclusively. As a matter of fact, the method according to the present invention is of very broad application and provides a full three dimensional (3D) dynamic motion analysis of the spine of a patient, including the neck, trunk and pelvis activity and the intersegmental movements.

Another object of the invention is also to provide a non-invasive equipment for carrying out this new method.

In accordance with a first embodiment of the invention especially designed for evaluating the flexibility of the lumbar portion of the spine of a patient in any plane (not exclusively off the sagittal plane), and thus detecting any discrepancy from a "normal" response that would help a medical doctor to establish and/or confirm a back pain diagnosis, a string of separate, dot-sized skin-markers which preferably consist of small LEDs fired under computer control, is fixed onto the skin of the back of the patient in the midline of his spine from at least cervical vertebra $C_7$ down to at least sacral vertebra $S_3$. Two other skin-markers are detachably fixed onto the skin of the back of the patient in a bilateral and symmetrical manner on the crests of his ilium.

A visualization equipment which preferably comprises a pair of cameras spaced apart from each other, is used to track, monitor and record the relative positions of all of the skin-markers on the back of the patient as he flexes forward in his sagittal plane.

The so recorded positions of the skin-markers fixed in the midline of the patient's back are then processed to determine the angle of flexion $\alpha$ of the patient as a function of time, this angle being indicative of the combined motion of both hip and spine of the patient. The recorded positions of the skin-markers symmetrically fixed on the ilium are simultaneously processed with the recorded position of the skin-marker fixed on the sacral vertebra $S_3$ to determine the angle of rotation "h" of the hip as a function of time, this angle "h" being indicative of the hip motion of the patient.

Then angle "h" is substracted from angle $\alpha$ to determine the actual contribution of the spine to the total flexion of the patient as a function of time, the contribution, expressed as angle "s", being indicative of the spine motion of the patient, and the values of angles $\alpha$, "h" and "s" are altogether processed to calculate the relative variations of "h" and "s" versus $\alpha$, which variations are respectively indicative of the ranges of hip and spine motions in the sagittal plane. After plotting, these variations are compared with each other and with results obtained from a group "normal" patients to determine any discrepancy or singularity.

From these comparison and determination, anyone skilled in the medical art may easily derive the requested information as to the flexibility of the spine and the presence of a potential mechanical injury therein.

It is worth mentioning that the same method may be used to collect numerous other data useful to evaluate the spine function as it moves freely in space, such as:
- the intersegmental mobility of the spine, i.e. the relative motion of a spinal segment with respect to the segment immediately below it;
- the segmental mobility of the spine, i.e. the orientation of each segment with respect to a plumb line (all segments are expected to move together toward the side of a bend, local reversal of motion being indicative of an abnormally below that level);
- general information on lateral bend, such as the segmental area sweep, area asymmetry, pelvic motion, thoracolumbar spine motion, bend area to midspine, trunk velocity intersegmental mobility and segmental mobility of the patient when the same is laterally bending in his frontal plane;
- the patient's torque as a function of the angle of flexion $\alpha$;
- the compression load at $L_5$ as a function of the trunk velocity;
- the power of the patient's torque
- the isokinetic response of the patient's spine, giving the torque values as a function of $\alpha$ at different speeds; and
- the isometric response of the patient's spine as a function of $\alpha$.

In accordance with a second embodiment of the invention especially designed for evaluating the flexibility of the cervical portion of the spine of a patient in any plane an thus detecting any discrepancy from a "normal" response that would help a medical doctor to establish and/or confirm a back pain diagnosis, a string of separate, dot-sized skin-markers which preferably consist of small LEDs fired under computer control, is fixed onto the skin of the patient's back in the midline of his spine from at least thoracic vertebra $T_5$ up to the skull. Other skin markers are detachably fixed in a bilateral and symmetrical manner on the skin of the patient's back on the crests of his scapulae, and on the rear of the patient's head.

A visualization equipment which preferably comprises a pair of cameras spaced apart from each other, is used to track, monitor and record the relative positions of all of the skin-markers on the back, neck and head of the patient as he flexes his neck in his sagittal and/or frontal plane(s).

The so recorded position of the skin-markers are processed to measure the scapula motion and evaluate its contribution to the neck motion; to measure the cervical spine motion; and to extract from the last measurement the intersegment and segmental mobilities of the cervical spine. All of these data as well as others such as the neck velocity, the percentage of cervical elongation, etc..., can then be compared with each other and with results obtained from a group of "normal" patients, to determine any discrepancy or singularity.

BRIEF DESCRIPTION OF THE DRAWINGS:

In the accompanying drawings:

FIG. 4 are curves showing geometric data on the trunk, spine and hip motion derived from the position of the skin-markers;

FIG. 9 are plots showing the geometric data obtained on a patient before and after rhizolysis;

FIG. 11 are plots showing the geometric data obtained on another patient before and after fusion;

FIG. 23 is a schematic representation of an equipment for use in carrying out the method according to the second embodiment of the invention.

DETAILED DESCRIPTION OF THE FIRST EMBODIMENT OF THE INVENTION

(a) general description of the equipment

Figure 1:
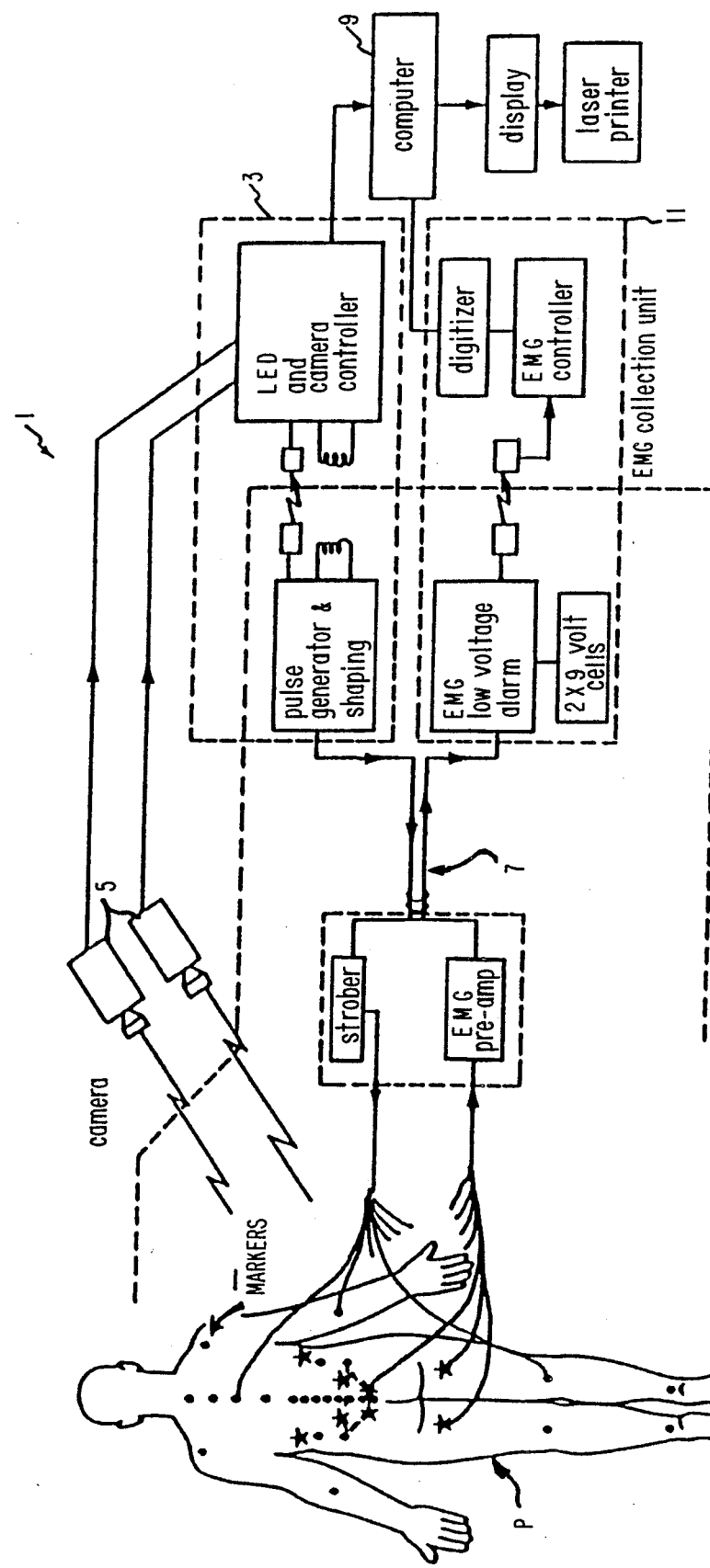
FIG. 1 is a schematic representation of an equipment for use in carrying out the method according to the first embodiment of the invention.

The non-invasive equipment 1 according to the first embodiment of the present invention, as shown in FIG. 1, is primarily designed to observe and record the spatial positioning of the lumbar portion of the spine of a patient "P" during a very specific exercise, namely executing lifts in the sagittal plane. The geometry of the spine of the patient during the exercise is deduced by measuring the position of 24 dot-shaped, skin markers fixed on the patient as shown with round dots in FIG. 1. Of the 24 markers, 12 are distributed along the back above the spine.

The markers are, in fact, small light-emitting diodes (LEDs) fired under computer control (see box 3) and tracked by two spaced-apart cameras 5. These markers are and must be very small in size. They are and must also be completely separate from each other in order to freely follow any motion or stretching of the patient's back without being affected by the muscular activity of this back, and thus to give a true and real indication of the actual position of the spine.

The uppermost LED in the patient's midline is preferably fixed on the spinous process of cervical vertebra $C_7$ or $T_1$ while the lowermost LED is fixed on a sacral vertebra, preferably $S_2$. Two other LEDs are also preferably positioned on the spinous process of thoracic vertebra $T_{11}$ and lumbar vertebra $L_4$, the other LEDs being merely put in between at regular interval. As a matter of fact, once some spaced-apart LEDs are set, the positions of the other LEDs with respect to the anatomical landmark, may be easily calculated from normalized anatomical tables.

Two of the remaining 12 markers are and must be positioned onto the skin of the back of the patient in a bilateral and symmetrical manner on the crest of the patient's ilium, at height substantially halfway between lumbar vertebrae $L_4$ and $L_5$ (which usually correspond to the height the ninth and tenth LEDs in the patient's midline).

The last 10 markers are merely used to track with the cameras 5 the general position of the patient while he is flexing forward. These last 10 markers are respectively fixed bilaterally and symmetrically onto the patient's shoulder at height substantially halfway between cervical vertebra $L_7$ and thoracic vertebra $T_3$, on the patient's back at height substantially halfway between thoracic vertebra $T_{11}$ and lumbar vertebra $L_1$, and on the patient's appendages (i.e. his legs and arms), above his elbows, below his knees and at his Achilles tendons.

During the exercise, the patient is free to move in an area 4×6 meters, thanks to an "umbilical cord" 7 or a telemetric system connecting the LEDs to their computer control 3. The LED markers are tracked by the cameras 5 with an accuracy of 1/500.

The three-dimensional coordinates of each marker are reconstructed by a computer 9 from the data generated by the two cameras 5. As the data is collected by the cameras at a speed of, say, 180 images per second, these can be combined to improve accuracy and still maintain an acceptable dynamic range at approximately 12 images per second.

Figure 2:
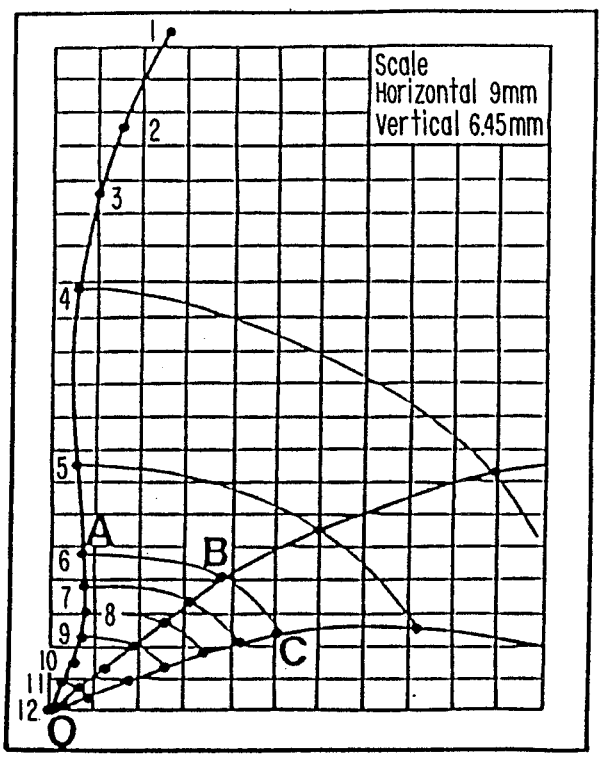
FIG. 2 is a representation of the true sagittal motion of the spine of a patient at different flexing position, obtained from a three-dimensional reconstruction of the positions of the skin-markers fixed on the spine of the patient with the, equipment shown in FIG. 1.

The reconstructed sagittal view of the position of the 12 markers placed above the spine in the patient's midline is shown in FIG. 2. These 12 markers define a curve which is an approximation of the true lumbar curve.

(b) angle of flexion α

By suitably processing the respective positions of the 12 markers fixed in the midline of the patient's back, one may easily determine the angle of forward flexion of the trunk of the patient as a function of time.

Figure 3:
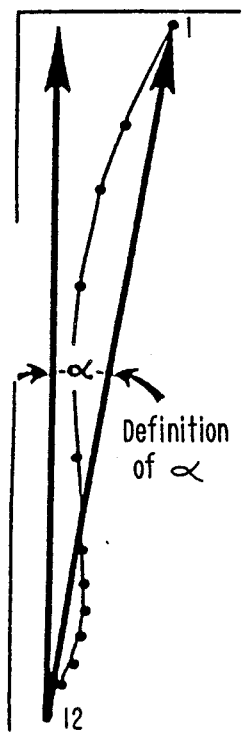
FIG. 3 is a sagittal representation of the skin-markers fixed on the spine of the patient, giving one possible definition for the angle of flexion $\alpha$ of the patient.

This angle α which is indicative of the combined motion of both the hip and spine of the patient, can be defined as the angle between an imaginary line passing through one of the uppermost LEDs in the midline of the patient's back and one the lowermost LEDs fixed on a sacral vertebra, and a vertical axis, as shown in FIG. 3. In such a case, processing can be carried out in the computer 9 by digitizing with an X-Y digitizer the relative positions of the selected markers, then calculating the slope of the line passing through these positions and deriving from this slope the value of α (the slope of the imaginary line being indeed equal to tangent α).

Alternatively, angle α can be defined as the angle between a mean-square fit line mathematically calculated as is known, from the relative positions of all the skin markers fixed on the patient's midline, and a vertical axis. Once again, the slope of this calculated line is equal to tangent α.

Angle α may of course be plotted or displayed as shown in FIG. 4 (see curve B).

(c) Hip motion

Simultaneously to the above processing, the recorded positions of the two skin-markers symmetrically fixed on the crests of the patient's ilium are processed in the computer 9 with the recorded position of the skin-marker fixed on one of the sacral vertebrae such as $S_2$ or $S_3$, to determine the angle of rotation "h" of the hip as a function of time. This angle "h" which is indicative of the hip motion of the patient, can be derived from the motion of the plane (see the dotted triangle on the patient in FIG. 1) defined by the abovementioned three markers.

The intersection of this plane with the sagittal plane yields a straight line. The angle between this line and the vertical characterizes the motion of the hip and can be plotted as shown in FIG. 4 (see curve C).

(d) Spine motion

Since the total motion characterized by the angle α is due to the combined motion of both spine and hip, the spine motion can be deduced by measuring the motion of the hip and substracting it from the motion of the trunk. In other words, the substraction of angle "h" from angle α permits to determine the actual contribution of the spine to the total flexion of the patient as a function of time. This contribution, which is hereinafter expressed as angle "s", is indicative of the spine motion of the patient and can be plotted as a function of time as shown in FIG. 4 (see curve D).

A very interesting peculiarity of the hip angle variation can be noticed in FIG. 4. During the first phase of the exercise, as the subject bends forward to pick up a barbell, the hip rotates forward to 30 degrees, then rotates backward to restrain the hips at an angle of about 15 degrees. This backward motion is due to the flexion of the knee as the subject squats to reach for the barbell. Nonetheless, the total trunk motion still increases, i.e. the spine motion has a predominant effect.

Figure 5:
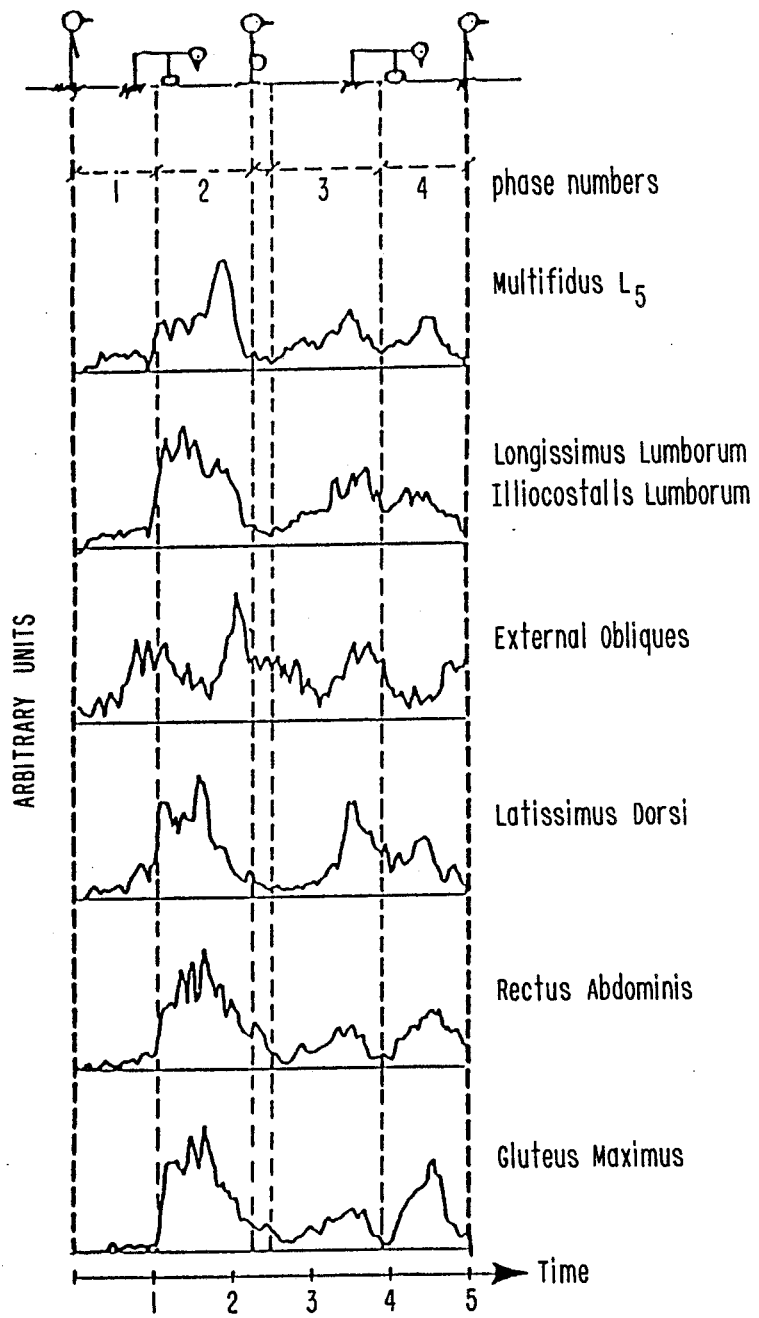
FIG. 5 are integrated electromyographic EMC) measurements of the activity of several muscles recorded with the equipment of FIG. 1 on a patient flexing forward a first time to lift up a barbell and then a second time to put it down.
Figure 6A:
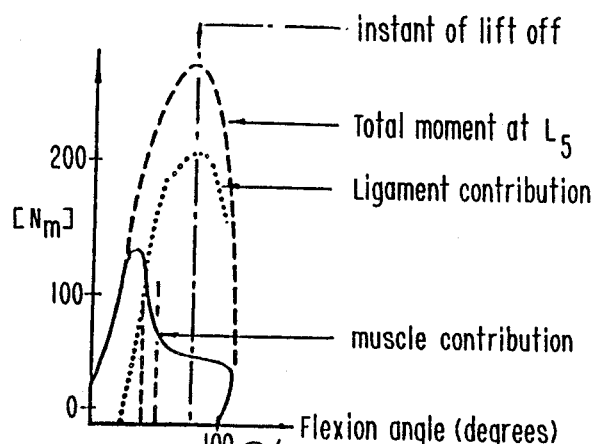
FIG. 6 are plots showing the geometric data plotted versus time in FIG. 4, now plotted versus angle $\alpha$.
Figure 6B:
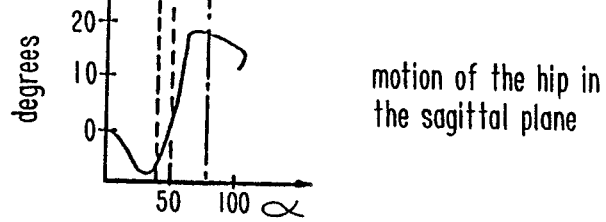
Figure 6C:
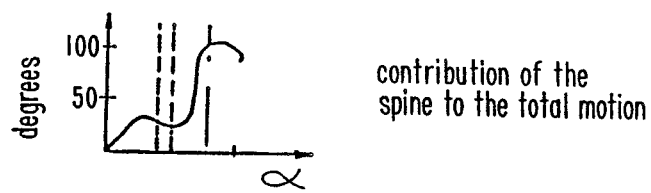
Figure 6D:
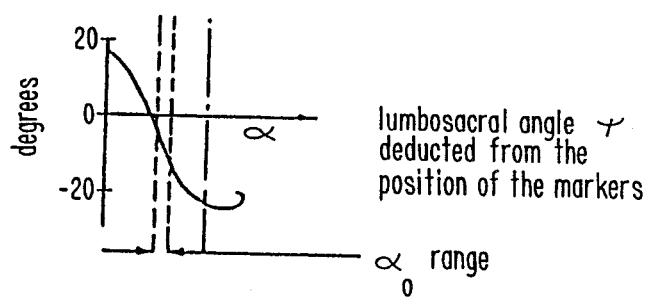

These laters are of course correlated with the spine motion (curve D), which is defined by the difference between the total trunk motion (curve B) and hip motion (curve C). As can be noticed, this spinal motion continues to increase even as the pelvis is restrained by the bending of the knees. This increase in spinal flexion is responsible for setting the posterior ligamentous system under tension, thus requiring no muscular contribution. This fact is by the way confirmed by measurements that may be simultaneously taken of the electromyographic activities of multifidus, iliocostalis, longissimus lumborum and rectus abdominis of the patient, as depicted in FIG. 5.

In accordance with the invention, the values of angles α, "h" and "s" are further processed to calculate the relative variations of "h" and "s" versus α. The variations which are respectively indicative of the ranges of hip and spine motions in the sagittal plane, are plotted or displayed (see FIG. 6) and may be used as accurate diagnosis tools by anyone skilled in the medical art to evaluate the flexibility of the spine and detect the presence of a potential mechanical injury in said spine. This diagnosis can very easily be made by comparing with each other the plots obtained for a given patient and, if necessary, comparing these plots with "standard" plots obtained from a group "normal" patients to determine any discrepancy or singularity.

As will be seen hereinafter (see the reported "cases"), the determination of the ranges of hip and spine motion in the sagittal plane, is sufficient as such to establish or confirm a diagnosis. However, further information such as the range of variation of the lumbo-sacral angle $\Psi$, the percentage arc elongation and/or the EMG activities of the patient's muscles, may also be obtained with the same equipment to confirm, complete and cross-check the basic data already obtained.

(e) Lumbo-sacral angle $\Psi$

The measurement of the lumbo-sacral angle $\Psi$ as a function of time while the patient is flexing, can be carried out by using the respective, recorded positions of the LEDs in the midline of the patient's back to mathematically reconstruct the true lumbar curve of the spine in the sagittal plane, then locating the inflexion point on the reconstructed curve, then tracing tangents to said inflexion points, and finally measuring the angle between these tangents, the so measured angle being defined as angle $\Psi$. The measured values of may then be processed by the computer 9 to calculate the relative variation of said angle $\Psi$ versus α. This variation of $\Psi$ versus α which is indicative of the lumbar lordosis of the patient's spine and thus directly correlated with the range of spine motion, can be plotted and the plot used as further information to detect the presence of a potential mechanical injury in the lumbar spine of the patient. Indeed, a decrease in $\Psi$ indicates a significant reduction in lumbar lordosis, as the spine straightens out (see FIG. 4, curve E).

One may of course wonder how the displacement of the markers correlates with the true lumbar curve derived from measurements that could be obtained from radiography. In practice, this correlation was checked by the inventor by taping 3 mm diameter steel balls over the spinous processes and the iliac crest. To control for image magnification of the X-ray machine, an one-inch diameter steel ring was taped above multifidus as close to the $L_3$ spinous process as possible. As this ring appeared as an ellipse on the film, vertebrae size might be scaled up or down until the shadow of the largest diameter of the ellipse is exactly one inch.

Figure 7:
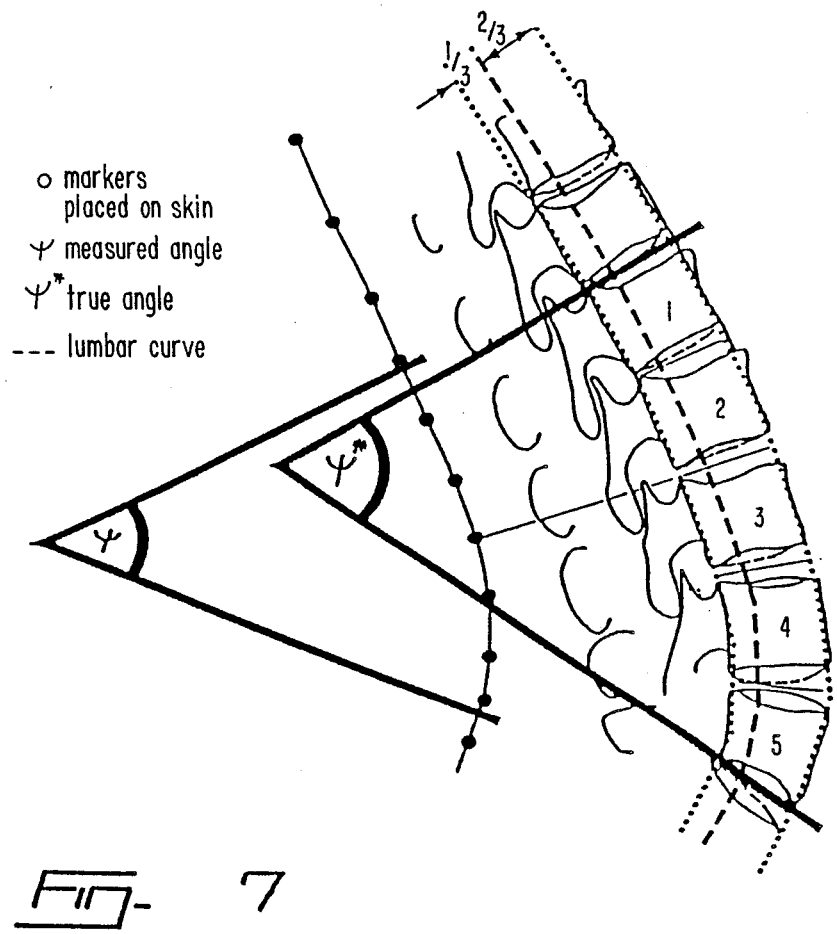
FIG. 7 is a sagittal view of the lumbar position of a spine in extension, showing the portion of the external markers vis-a-vis the actual position of the vertebrae drawn from a X-ray film.
Figure 8:
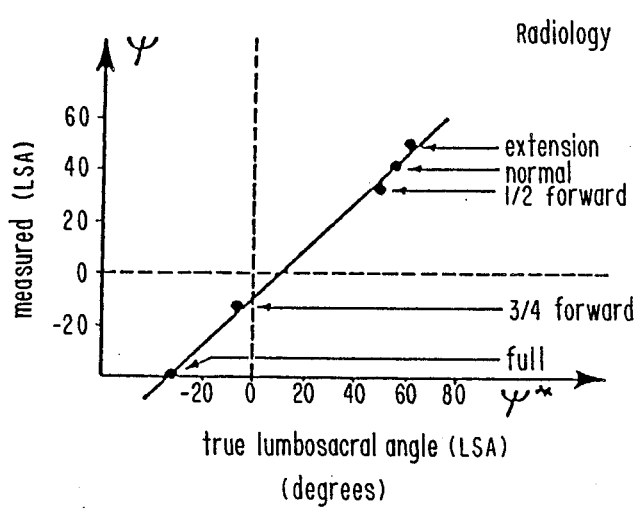
FIG. 8 is a plot showing the relation existing between the lumbo-sacral angle $\Psi$ as measured by the markers and the true lumbo-sacral angle Ψ* as obtained by X-rays for five different values corresponding to five different postures.
Figure 10A:
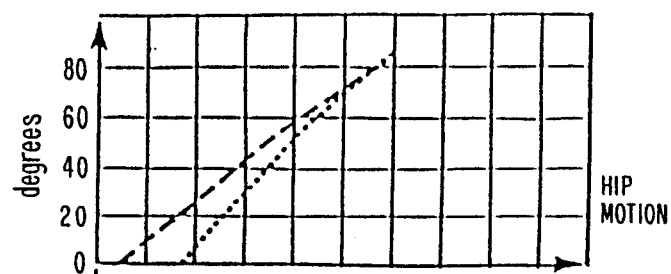
FIG. 10 are plots showing the geometric data obtained on a patient before and after fusion.
Figure 10B:
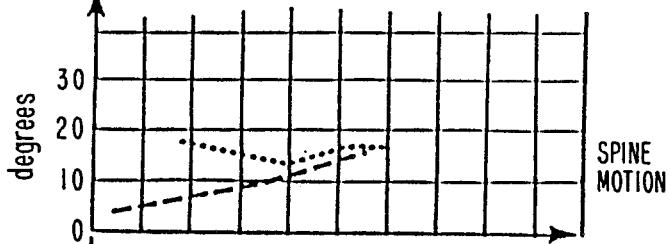
Figure 10C:
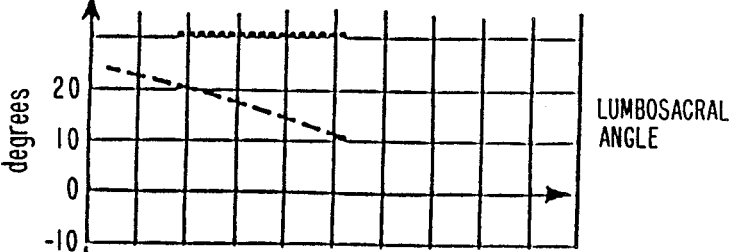
Figure 10D:
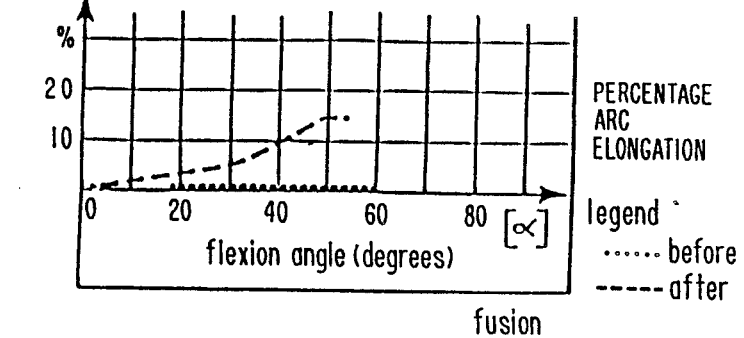
Figure 12A:
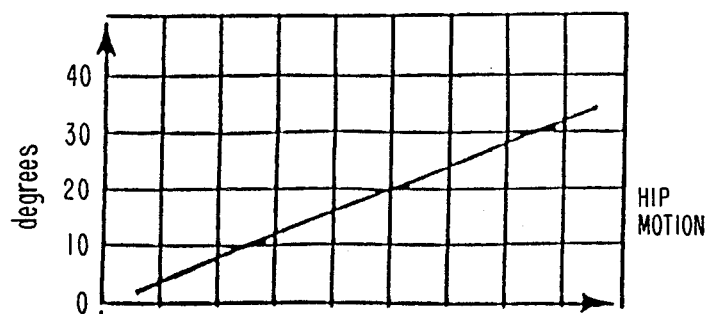
FIG. 12 are plots showing the geometric data obtained on a healthy patient possibly malingering.
Figure 12B:
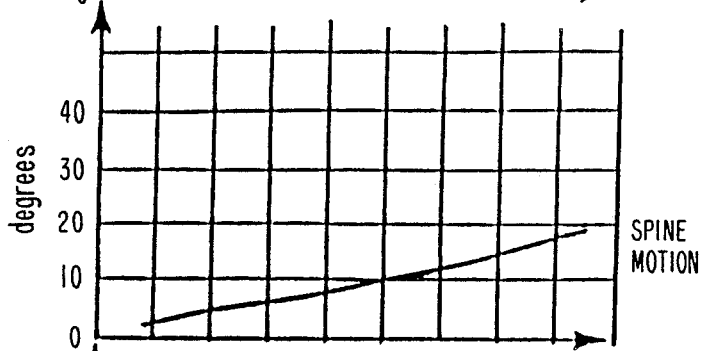
Figure 12C:
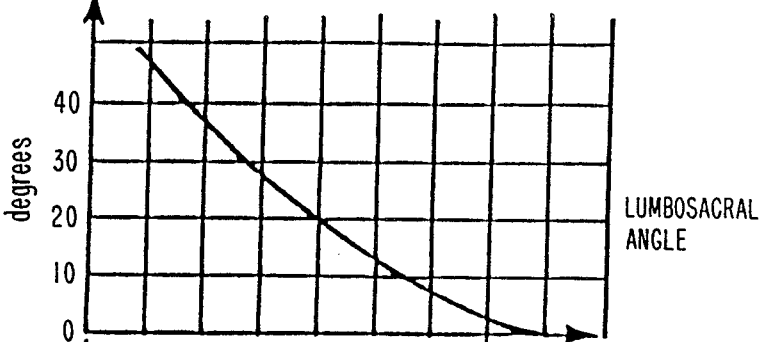
Figure 12D:
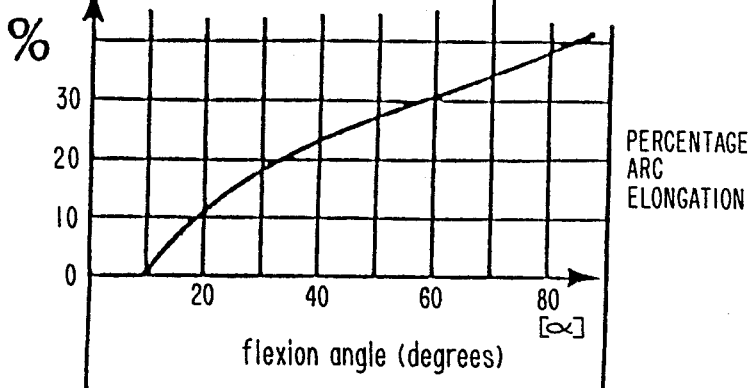
Figure 13A:
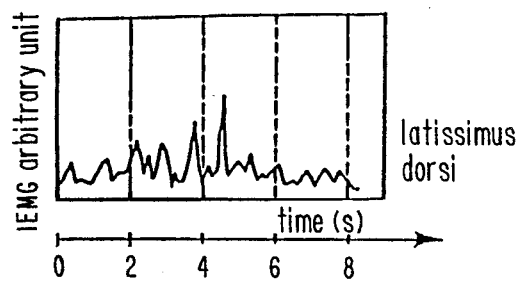
FIG. 13 are plots showing the geometric data obtained on a patient having a torsional injury.
Figure 13B:
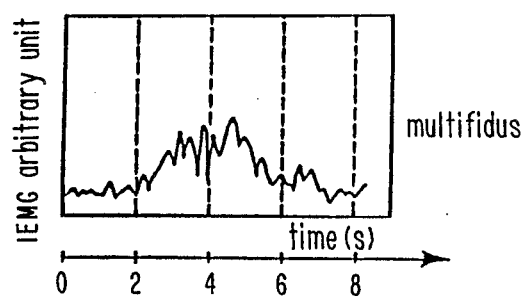
Figure 13C:
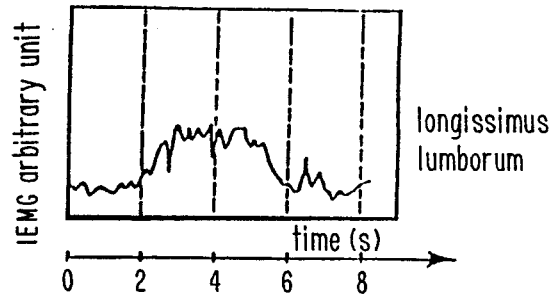
Figure 13D:
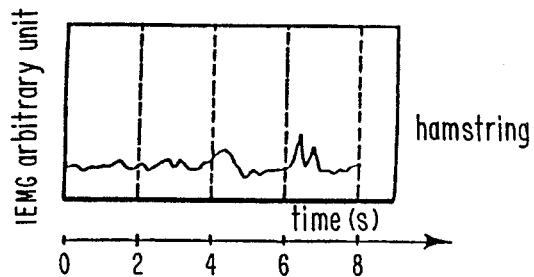
Figure 14:
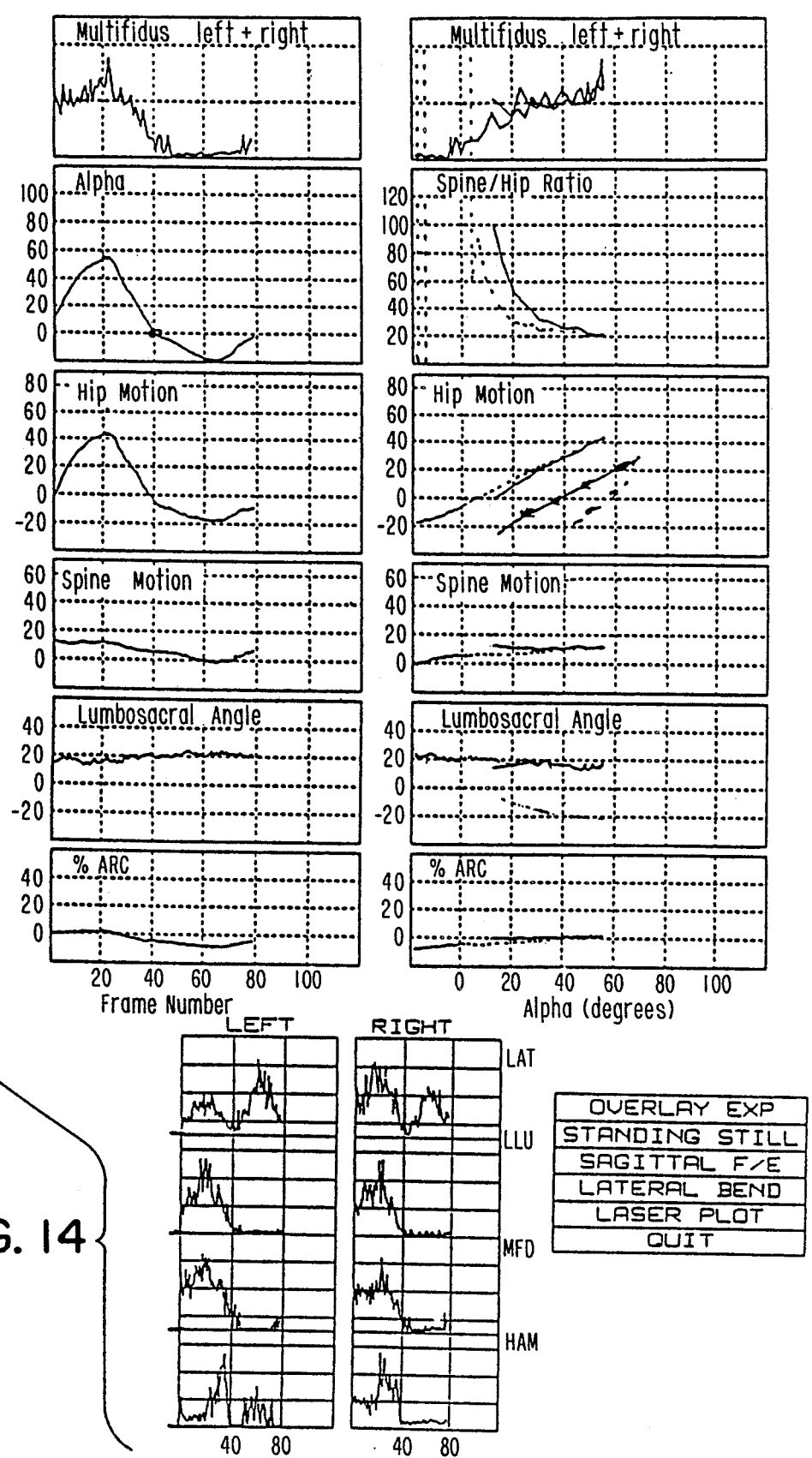
FIG. 14 is a typical example of Report that may be obtained with the equipment shown in FIG. 1.

By taking several lateral radiographs of the subject so instrumented (in the erect stance and for 15,30,45,60 and 90 degrees of forward flexion), a fair idea of the relationship between the position of the markers and the vertebrae was obtained (see FIG. 7). In practice, the skin motion (i.e. the displacement of the marker vis-a-vis a given spinous process as the subject bends forward) has proved to be small (a few millimeters) and unimportant because the skin motion is in the sagittal plane. In other words, displacing a marker in that direction had little measurable effect on the calculated value of the angle $\Psi$. Since the true lordosis and the curve defined by the markers are uniquely related, there is no need to measure the true lordosis to interpret the data. Therefore, it is justified to use $\Psi$ instead of the true lumbo-sacral angle $\Psi^*$ (defined as the angle between the bisectors of $T_{12}/L_1$ and $L_5/S_1$) as clearly evidenced by FIG. 8 which shows a linear correlation between these two angles, the error in measurement of the position of the markers vis-a-vis the bony structure being about ±1.5 mm.

Thus, the above reported data demonstrates that external measurements using markers placed on the skin can give a reasonable approximation of the true lordosis or lumbo-sacral angle.

(f) Percentage arc elongation

The measurement of the percentage of elongation of the arc sustained by the skin markers while the patient is flexing, can be carried out by using the respective, recorded positions of the markers in the midline of the patient's back to mathematically reconstruct the true lumbar curve of the spine in the sagittal plane (see FIG. 2) and then measuring the distance along the curve between the markers. Then, the measured values of percentage arc elongation may be processed by the computer 9 to calculate the relative variation of elongation versus α. This variation which is indicative of the lumbar lordosis of the patient's spine and thus directly correlated with the range of spine motion, can of course be plotted (see FIG. 4, curve F) and used as further information to detect the presence of a potential mechanical injury in the lumbar spine of the patient.

The effect of the reduction in lumbar lordosis on the rotation of the intervertebral joint is illustrated in FIG. 4 (curve F). In this example, the distance between markers #12 (point zero) and #6 (point A) was 113 mm when the subject adopted an erect, relaxed stance (see FIG. 2). This distance increased to 153 mm (point B) and eventually extended to 170 mm (point C) when the subject was fully bent and touching the barbell.

From the percentage increase plotted in this FIG. 2 (curve F), it is evident that this increase mirrors the variation in the lumbo-sacral angle $\Psi$ (see curve E). It should be noted that the 50 per cent increase in the distance OA is quite significant, as it allows the posterior ligamentous system (PLS) to be stretched. That this subject is able to rotate all his intervertebral joints during forward flexion is also evidence that they ought to be in good condition and therefore permit the PLS to play its important role. The subject was also tested at a weight of 60 kg with similar results, thus indicating that his lifting capacity exceeds 60 kg.

(g) EMG activity

The measurement of the electromyographic (EMG) activities of the patient's muscles can be carried out by detachably fixing a set of surface electrodes (shown with stars on the patient P in FIG. 1) bilaterally on the latissimus dorsi below scapula, the longissimus lumboruni at vertebra $L_3$, the multifidus at $L_5$ and the hamstring semitendinosus. Alternatively, the EMG data may be collected bilaterally on the multifidus (2 cm off the midline at $L_5$ level), on the iliocostalis and longissimus lumborum (at 5 cm off the midline at $L_3$). on the external obliques above the triangle of Petit, on the latissimus dorsi at $T_5$ and on the rectus abdominis at the $L_3$ level. The raw EMG signals that are recorded are band filtered (5 Hz to 300 Hz), digitized at 1 KHz and rectified (at 11) and integrated in the computer 9 to determine the magnitude of activity of every muscle, and the integrated signals plotted as a function of time.

The plots obtained on the left and right sides of the patient may be compared to detect any discrepancy, and this information as well as the general muscle activity as reflected by all of these EMG plots may be used as a further information to detect the presence of a potential mechanical injury in the lumbar spine of the patient.

FIG. 5 shows the integrated EMG (IEMG) of several muscles recorded during a very specific exercise comprising four distinct phases:

1. from a relaxed upright stance the patient bended forward to pick up a weight (a 20 kg barbell). The knees might or might not be locked, depending upon the person's choice;

2. the barbell was then lifted. The patient returned to the upright posture, keeping the barbell at arm's length in such a way that the arms always hang down from the shoulders;

3. the patient bended forward again to put the weight down; and 4. he returned empty-handed to the upright stance.

FIG. 6 clearly shows how the plotting of the IEMG may be complementary helpful to make a diagnosis. Curve A of this FIG. 6 was derived by scaling and superimposing the IEMG of the multifidus with the calculated moment at L. The muscle relaxation phenomenon is obvious. Indeed, one may note the sharp drop in muscle contribution at the very instant it is needed most, according to the school of thought proposing that back muscles do the lifting. This of course supports the inventor's mathematical representation of the spine anatomy and mechanics as shortly reported hereinabove in the preamble of the specification.

(h) Intersegmental mobility

By suitably processing in the computer 9, the recorded positions of the skin-markers fixed in the midline of the patient's back, one can easily determine and measure the relative motion of each of the skin-markers with respect to the skin-marker immediately below it. The so measured values of the relative motions of the skin-markers during the flexion step and the subsequent extension step respectively are, in practice, indicative of the contribution of each spinal segment to the flexibility of the spine in the lumbar region (see the resulting diagram in the upper right corner of FIG. 16).

(i) Other available information

As already indicated hereinabove, the equipment according to the invention can also be used to collect numerous other data useful to evaluate the spine function as it moves freely in space.

By way of example, the equipment 1 disclosed hereinabove can be used to determine:
- the patient's torque as a function of the angle of flexion $\alpha$;
- the compression load at $L_5$ as a function of $\alpha$;
- the trunk velocity;
- the power of the patient's torque;
- the isokinetic response of the patient's spine, giving the torque values as a function of $\alpha$ at different speeds; and
- the power versus velocity.

The same equipment may also be used for evaluating the flexibility of the spine on lateral bends, by determining:
- the segmental areas sweep, (i.e. the area swept out by the spine while it moves through the space away from its resting position);
- the area asymmetry (i.e. the amount of asymmetry in the area swept by each segment of the spine during its right and left movements);
- the pelvic motion;
- the pelvic contribution to the patient's motion as the trunk bends sideways;
- the thorax, columnar spine motion (i.e. the contribution of the lumbar and thoracic spine to the total trunk;
- the bend area to mid-spine (i.e. the variation in the area swept by the total lumbar spine away from its resting positions as the patient swings from right to left);
- the trunk velocity (i.e. the speed of the trunk, beginning at zero in the initial resting position and returning to zero in the final resting position as the patient bends sideways);
- the segmental mobility of the spine (i.e. the orientation of each segment with respect to a plumb-line, all segments being expected to move together toward the side of the bend and, accordingly, local reversal of motion being indicative of an abnormality below that level).
- the intersegmental mobility of the spine (i.e. the relative motion of each spinal segment with respect to the segment immediately below it); and
- the same information as above when the pelvic contribution to the lateral bend has been removed.

Of course, further general information may be obtained, such as, for example, an anteroposterial view of the patient while standing still, a lateral view of the same patient while standing still, and an average gross range of motion of the trunk over one or more tests as a patient flexes forward and/or bends sideways.

(j) Clinical evaluation

Of course, all of the objective data obtained with the method and equipment according to the invention may (and must) be correlated with the results of a clinical evaluation carried out by asking the patient to answer a set of psychological questions describing his pain in such specific situations as walking, sitting and lying down.

The answers may be used to determine, in broad terms, whether or not the pain is mechanical in nature (e.g. radicular, somatic, etc.) or of another origin (e.g. neoplastic, viscerogenic, etc.). Other tests that may also be performed are: the Oswestry low back pain disability questionnaire, the waddell inappropriate symptom test, the Mooney-Wiltse pain drawing, the Dallas pain drawing and assessment, the pain intensity and linear pain scale, and the Million visual analog scale.

(k) Methodology

A practical way of reducing into practice the method according to the invention and taking advantage of all of its features is as follows.

In a first step, the patient is requested to complete a preselected questionnaire that may be memorized in the computer, in order to obtain the clinical evaluation necessary for correlation purpose [see chapter (j) hereinabove].

In a second step, the patient is harnessed with the LED markers and the EMG electrodes of the equipment [see chapter (a) hereinabove].

In a third step, the patient is requested to perform the simple tasks of flexing forwards and extending back and, if desired, laterally bending in one way and the other and/or lifting weights, while the LED markers are fixed and their relative positions are tracked by the cameras 5. During the same period the EMG activity is measured and recorded.

Last of all, in a forth and last step, the compiled data stored in the computer can be reviewed at the physician's convenience on the monitor display unit and printed if desired.

The kind of information that is available with this technique is shown in FIGS. 15 to 22. It is worth mentioning that this information can be used not only for evaluating the flexibility of a patient's spine and detecting an injury therein but also evaluating his progress during the course of physiotherapy or determining the duration of a physiotherapy program.

The first information that can be displayed and printed out, is a general overview showing the position of the markers relative to anatomical land marks and the gross range of motion in flexion, extension and lateral bending.

Figure 15:
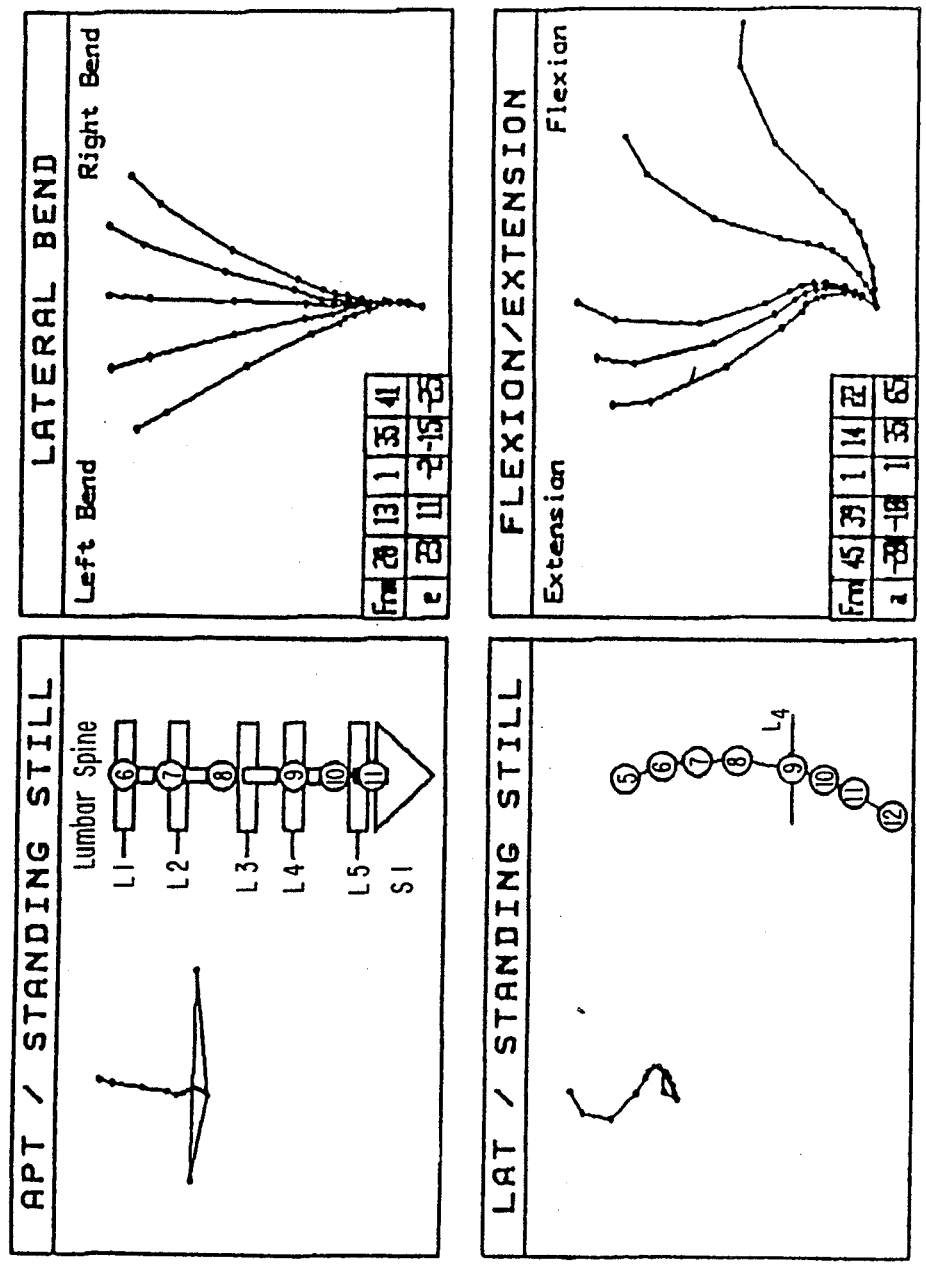
FIGS. 15 to 22 are other examples of Reports that may be obtained with the equipment shown in FIG. 1.

As clearly shown in FIG. 15, an anteroposterial view of the patient while standing still can be displayed. A lateral view of the patient while standing still may also be displayed. In both cases, an enlarged view of the position of the markers relative to the major anatomical landmarks of the lumbar spine can be obtained. The average gross motion of the trunk (thoracolumbar spine and pelvis) over one or two tests as the patient stands sideways may also be displayed, together with the average gross range of motion of the trunk while the patient is flexing forwards and extending back.

Figure 16:
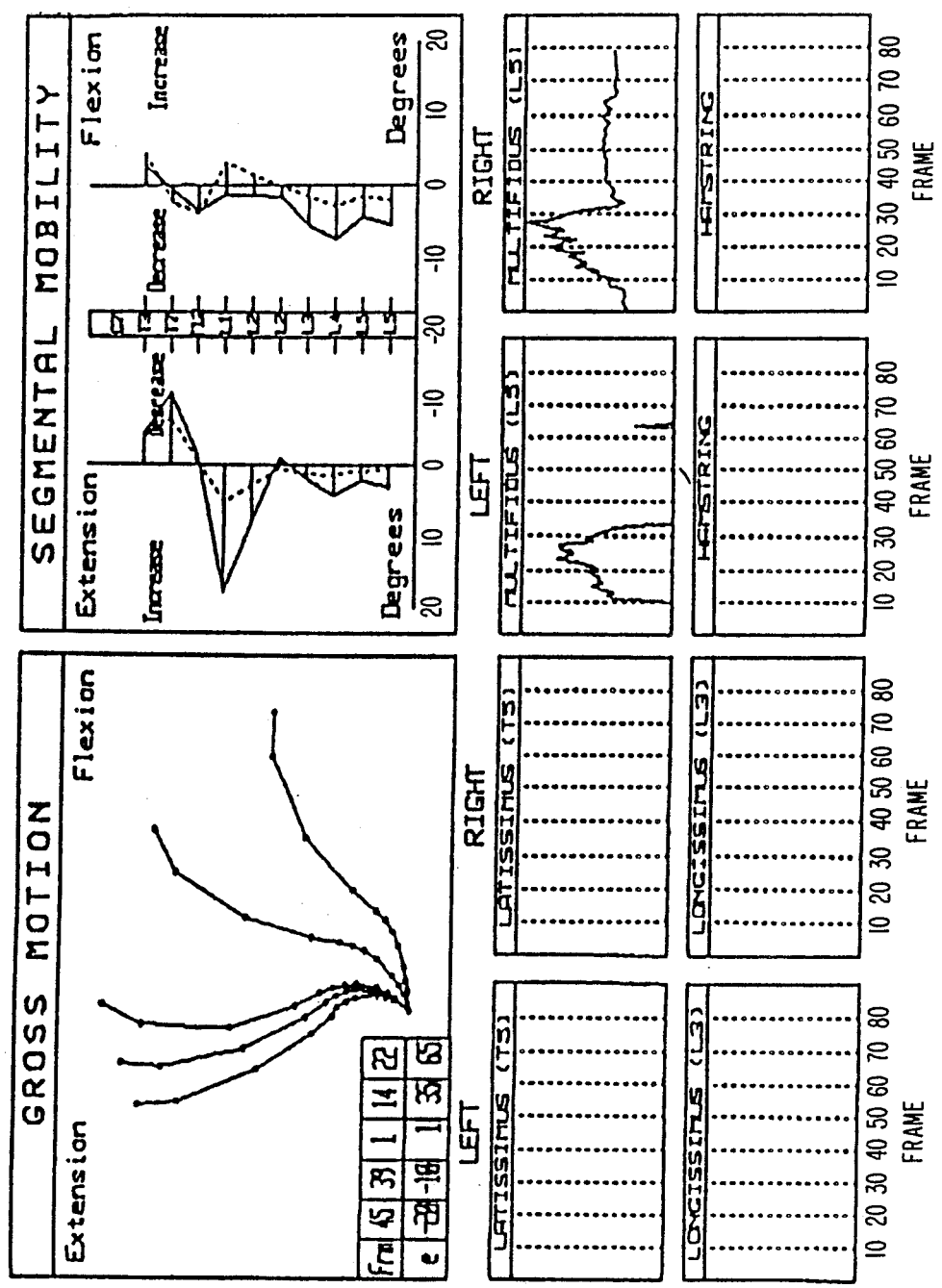

Then, the flexion/extension segmental motion and muscular activity may be displayed, as shown in FIG. 16. In this figure, the average gross range of motion of the trunk is displayed again for reference purpose. The intersegmental mobility is also displayed as well as the bilateral activity of the multifidus at $L_5$.

Figure 17:
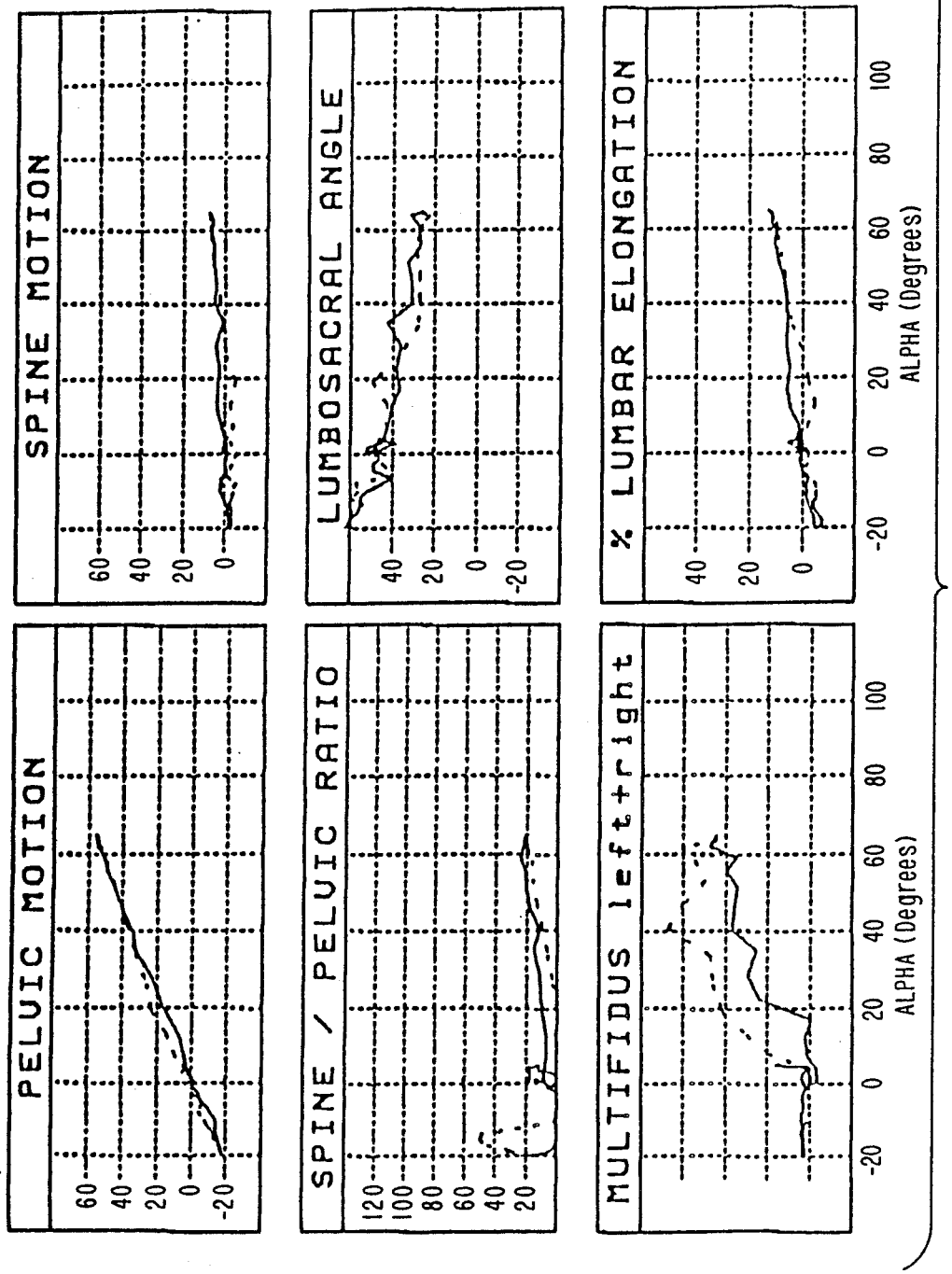
Figure 18:
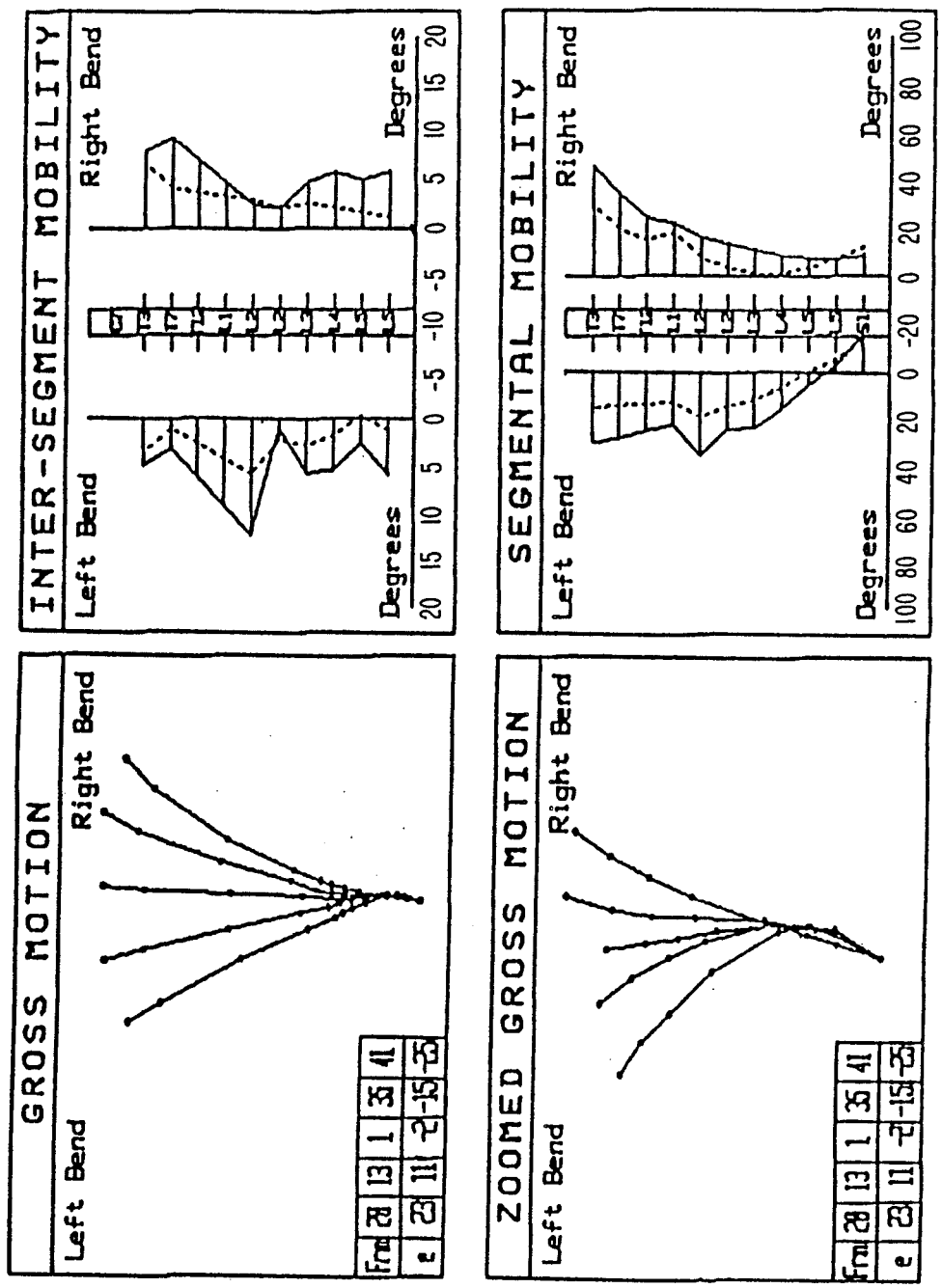
Figure 19:
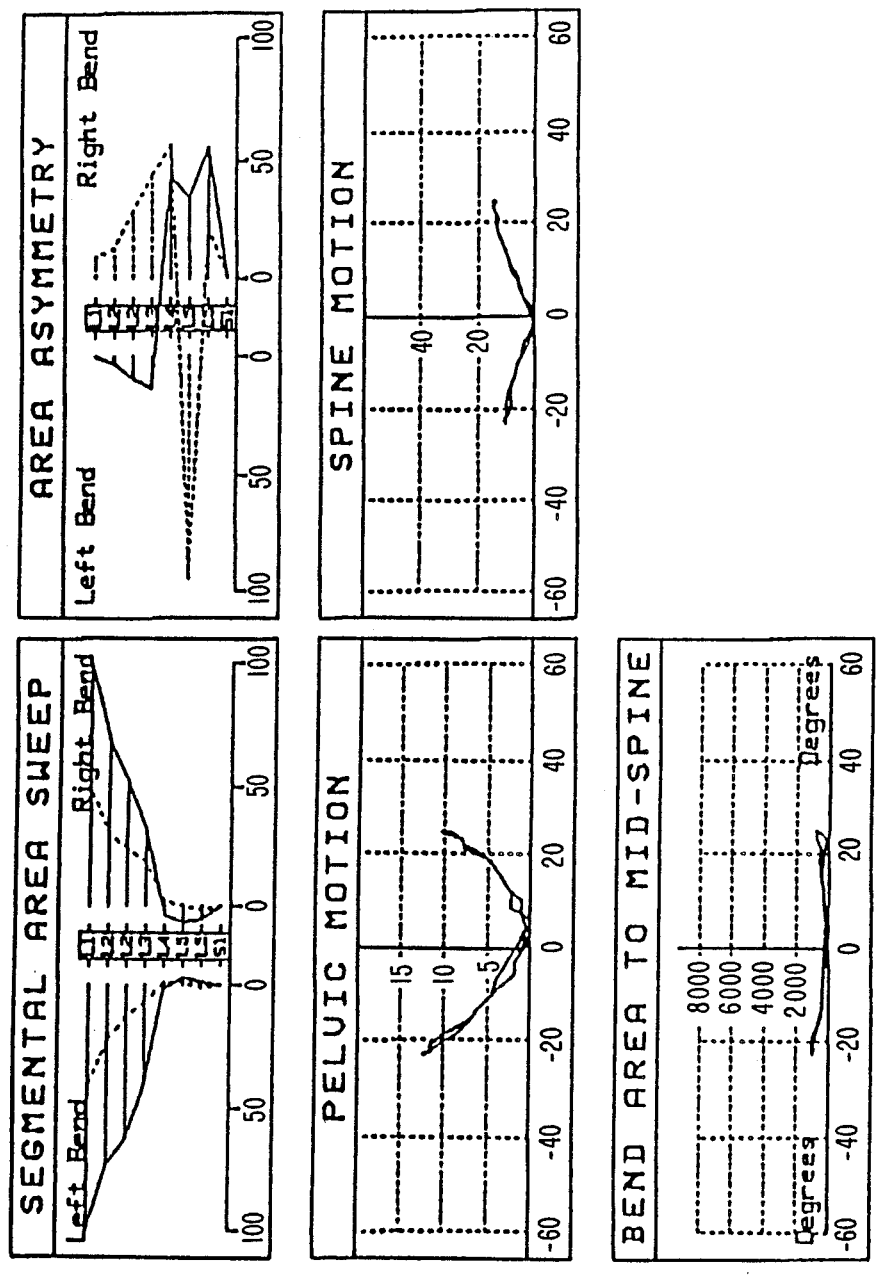
Figure 20:
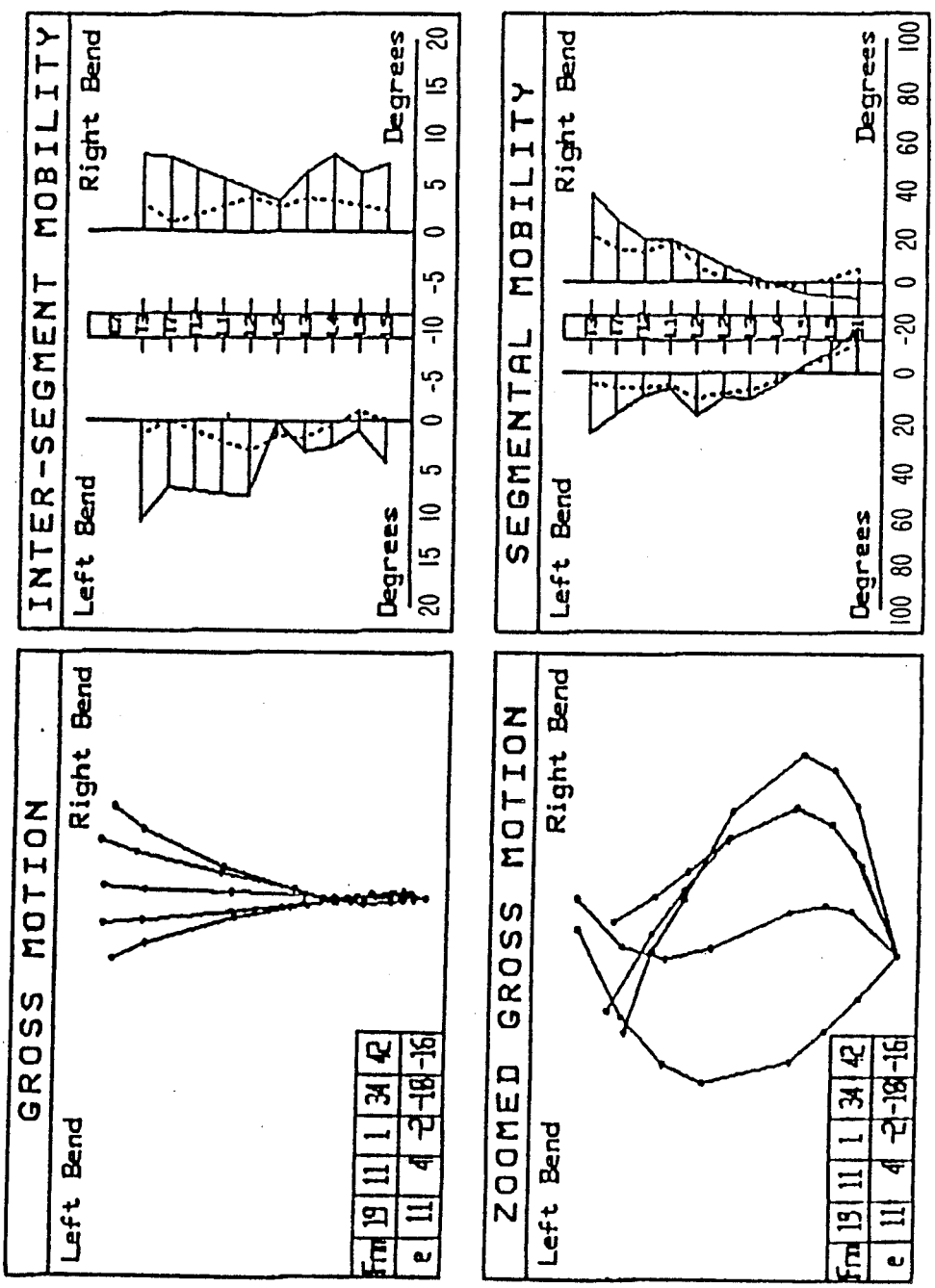
Figure 21:
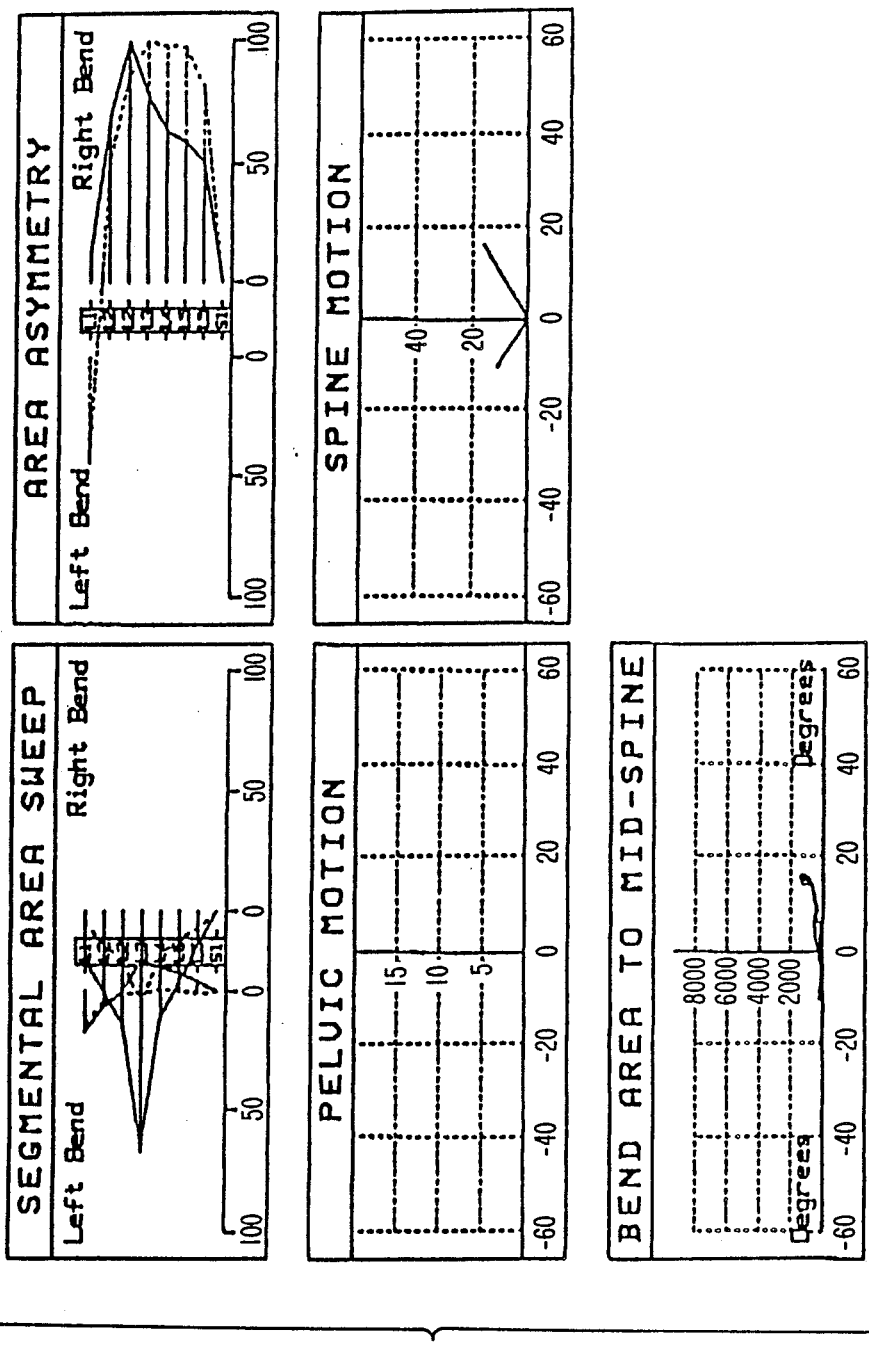

Then, the practitioner may call the more relevant information, namely the relative contribution of the spine and pelvis to the total trunk motion in flexion and extension. This information that is shown in FIG. 17 includes:

the pelvic motion (i.e. the contribution of the pelvis to the total trunk motion);

the thoracolumbar spine motion (the contribution of the lumbar and thoracic spine to the total trunk motion);

the spine to pelvic ratio;

the variation of lumbosacral angle;

the percent of lumbar elongation; and the multifidus activity (the muscular activity of multifidus is not a reliable indicator in itself; however, the presence of muscle relaxation phenomenae indicates posterior spinal ligament elongation and good individual intervertebral motion).

FIGS. 18 to 21 show further information that may be obtained with the same equipment when the task performed by the patient is to bend sideways in his frontal plane.

Figure 22:
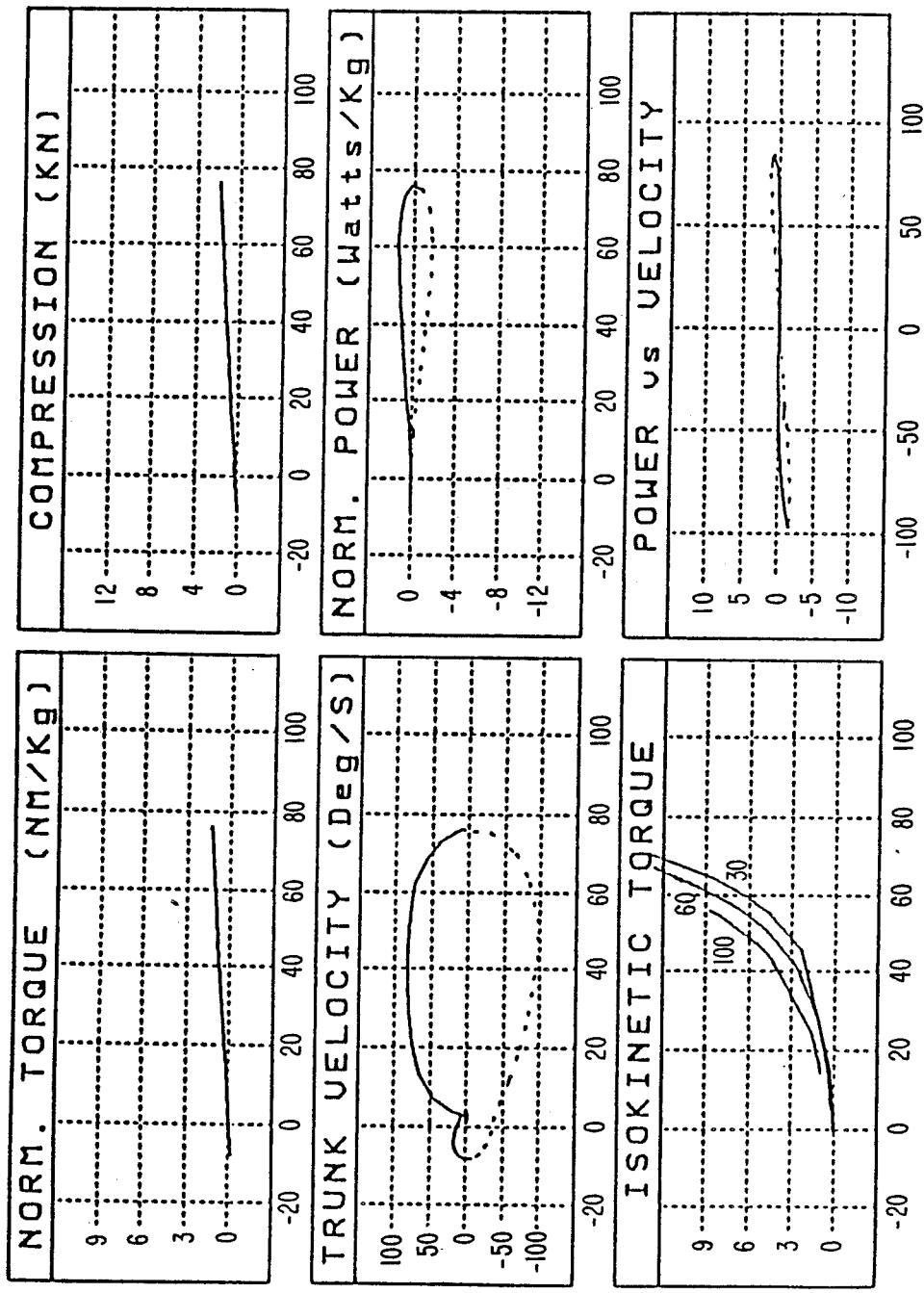

Other information that may be obtained with the equipment and be subsequently displayed and printed out is shown in FIG. 22. The information displayed in this figure can be easily derived by calculations carried out within the computer 9, based on the relative positions of the skin-markers during the flexion/extension test, taking into account the velocity of the patient. This additional information includes:

the patient's torque as a function of the angle of flexion $\alpha$;

the compression load at $L_5$ as a function of the trunk velocity;

the power of the patient's torque;

the isokinetic response to the patient's spine, giving the torque value at the function of $\alpha$ at different speeds of flexion/extension; and the power of patient's torque as a function of his velocity.

(l) EXAMPLES

The equipment 1 according to the invention as disclosed hereinabove was used to collect data on a plurality of individuals known to have spinal injuries. The various cases reported hereinafter will clearly show how the collected data may be used as diagnosis tools to evaluate the flexibility of the spine and detect any mechanical injury therein.

CASE #1:

A patient with a facet syndrome resolved by rhizolysis

This patient was tested by the equipment 1 according to the invention in October 1986. He was asked to flex forward as far as possible without lifting a load. The collected data are shown in FIG. 9 and may be compared with those shown in FIG. 6, which may be considered as representative of a "normal" response.

This subject was reluctant to bend fully forward using spinal flexion. Here, the hip motion is equally important. In November 1986, the subject underwent a procedure called rhizolysis, in which the nerves feeding both right and left facets at $L_4$ were burned. This is equivalent to disconnecting the local "alarm system" (and therefore the pain) without changing anything in the mechanical structure.

The same patient returned to our laboratory in January 1987 for another evaluation. As his pain was reduced by 50% (according to the subjective evaluation), and he was very happy. Nevertheless, the collected data shows almost no difference in spinal motion. This confirms the nature of the rhizolysis procedure. The level of functionality of his spine did not change.

CASE #2:

A patient with a clinically diagnosed disc injury at $L_5/S_1$, resolved by intervertebral body fusion (anterior approach) —a successful case.

This patient was evaluated by the equipment according to the invention February 1987 (see FIG. 10). His data show restricted spinal motion, with almost no measurable variation in his lumbo-sacral angle (notice the almost flat response of the lumbo-sacral angle before surgery). The pain was so intense that the entire spine was rotating as a unit around the acetabulum. Following surgery and the fusion of $L_5/S_1$, the entire lumbar section recovered a significant amount of mobility. The patient's psychological scores also show improvement. This is believed to be a successful case.

This is a paradoxical result that may be due to the relief in pain at $L_5S_1$ which allowed the upper section of the spine to move more freely. This surgical intervention was, therefore, successful in the sense that it 10 improved the range of motion of the spine and, it is believed, its functionality.

It was noted, however, that other fused patients who were tested exhibited considerable reduction in spinal functionality. The benefits of spinal fusion are debated rather vigorously in the literature. There seems to be as many successes as failures, with no coherent explanation as to why this is so. The equipment according to the invention sees successes and failures in terms of functionality and, in that sense, represents an objective method of evaluating the benefits of surgery. It could also be argued that the anterior approach which was chosen for the fusion did not require cutting through the PLS and any of the erectores. Hence, this patient kept his ligamental system intact which is believed to be an important reason for this success.

CASE #3:

A patient with a classically diagnosed multiple injury at $L_{4/5}$ failed chemopapain (resolved by fusion)—a less-than-successful case.

This patient was fused from $L_4$ to $S_1$. The significant loss of range of motion that resulted from the fusion, proved that the case was less than successful. The EMG of multifidus shows erratic data, demonstrating extensive damage to the muscle (see FIG. 11). Because this patent was fused using a posterior approach, extensive damages to the PLS and the erectors resulted, hence the difficulty of the patient to regain a normal range of motion.

CASE #4:

Symptom exaggeration—possible malingering.

A patient examined with the equipment according to the invention in March 1987 scored randomly on the various psychological tests. Objective data on his spine motion demonstrated a very good, almost normal response. Lateral bending demonstrated a small residual problem at $L_{4/5}$, possibly from a fresh torsional injury (see FIG. 12).

The conclusion in this case was that the patient demonstrated objective signs, most likely due to a small torsion injury at $L_{4/5}$, which was demonstrated by examination of the lateral bending response. This injury does not interfere significantly with spinal functionality. The randomness of his scores on the psychological tests may point out an attempt to exaggerate the symptoms in order to obtain better compensation for his real injury.

CASE #5:

Torsional injury at $L_{4/5}$-EMG response in flexion-extension.

This patient had occasional back pain two years before this recording was made (FIG. 13). The clinical diagnosis was torsional injury at $L_{4/5}$.

The data demonstrate a complete lack of confidence in the ability of the spine to flex. The maximum percentage of elongation was 10%. The EMG responses of multifidus and illiocostalis and longissimus lumborum confirm the patient's reluctance to trust his PLS and flex his spine. The erectores immediately fire as a group as soon as the forward flexion begins. This is a characteristic response which should be compared with FIG. 5.

The lateral bending test demonstrates a reluctance to bend the spine to the right. This refusal can be explained by the need to prevent lateral bending of $L_{4/5}$ so that no axial torque in the direction of the initial injury is induced.

DETAILED DESCRIPTION OF THE SECOND EMBODIMENT OF THE INVENTION

The non-invasive equipment 1' according to the second embodiment to the present invention as shown in FIG. 23, is primary designed to observe and record spatial positioning of the cervical portion of the spine of a patient "P'" while the patient is flexing his head forwardly and backwardly and/or bending it sideways.

The geometry of the cervical portion of the patient's spine during the exercise(s) may be deduced by measuring the position of a minimum of seven dot-shaped, skin-markers detachably fixed onto the skin of the back and neck of the patient in the mid-line of his spine from at least thoracic vertebra $T_5$ up to the skull.

As in the first equipment, the markers are preferably small light emitting diode 5 fied under computer control (see box 3') and tracked by two spaced-apart cameras 5' (to obtain a spatial vision of the marker).

In order to properly determine the actual contribution of the cervical portion of the spine to the total head motion, at least two other skin-markers are detachably fixed to the skin of the back of the patient in a bilateral and symmetrical manner of the crests of his scapulae. Moreover, in order to determine the position of the head during measurement and properly assessing its angle of inclination, at least two further skin-markers may be detachably fixed onto the rear of the head of the patient in a bilateral and symmetrical manner.

During the exercise, the patient is free to move due to an umbilical cord 7' or a telemetric system (not shown) connecting the LED to the computer control 3' via a strober.

The three dimensional coordinates of each marker are reconstituted by a computer 9' from the data generated by the two cameras 5'.

By suitably processing the respective positions of all the skin-markers tracked by cameras on the back, neck, head of the patient while the same moves his neck, it is possible to measure the scapula motion and evaluate its contribution to the neck motion. It is also possible to deduct from this first information the cervical spine contribution to the total neck motion. It is further possible to extract from the measured value the cervical spine motion, the intersegmental and segmental mobilities of the cervical spine.

All of these data may be plotted.

By comparing the plots with each other and with plots obtained from a group of "normal" patients substantially as explained hereinabove, it is possible to determine any discrepancy or singularity and derives from this comparison and determination the requested information as to the flexibility of the cervical portion of the spine and/or the presence of potential mechanical injuries therein.

Although the masculine pronoun has been used exclusively hereinabove and in the following claims, it has to be interpreted as including the feminine.

The embodiments of the invention in which an exclusive property or privilege is claimed are defined as follows:

1. A non-invasive equipment for the evaluation of the flexibility of the spine of a patient and, as a result of this evaluation, the detection and identification of possible mechanical injuries in the cervical portion of said spine, said equipment comprising:
   (a) a plurality of separate, dot-sized skin-markers attachable to the skin of the back and neck of the patient in the mid-line of a spine from at least thoracic vertebra T-5 up to the skull;
   (b) two other dot-sized skin-markers attachable to the skin of the back of the patient in a bilateral symmetrical manner of the crests of his scapulae;
   (c) two further dot-sized skin-markers attachable to the rear of the head of a patient in a bilateral and symmetrical manner;
   (d) visualization equipment means comprising two spaced-apart cameras for tracking and monitoring the relative positions of all of the skin-markers on the back, neck and head of the patient as a patient moves his neck;
   (e) means connected to said visualization equipment means for recording the monitored positions of the skin-markers;
   (f) means for processing the so-recorded positions of the skin-markers to measure the scapulae motion and evaluate its contribution to the neck motion;
   (g) means for further processing the recorded positions to the skin-markers to measure the cervical spine motion;
   (h) means for extracting from the measured cervical spine motion the segment and intersegmental mobilities of the cervical spine; and
   (i) means for plotting the processed and extracted data.

2. An equipment for the non-invasive evaluation of the flexibility of the spine of a patient and, as a result of this evaluation, the detection and identification of possible mechanical injuries in the lumbar portion of said spine, said equipment comprising:
   (a) a plurality of separate, dot-sized skin-markers attachable to the skin of the back of the patient in the midline of his spine from at least cervical vertebra C7 down to at least sacral vertebra S3;
   (b) two other dot-sized, skin-markers attachable to the skin of the back of the patient bilaterally and symmetrically on the crests of the ilium of said patient;
   (c) a visualization equipment means for observing and monitoring the relative positions of all of said skin-markers on the back of the patient as he flexes forward in his sagittal plane;
   (d) means connected to said visualization equipment means for recording the monitored positions of the skin-markers as the patient is flexing forward;
   (e) means connected to the recording means for processing the recorded positions of the skin-markers fixed in the midline of the patient's back to determine the angle of flexion $\alpha$ of the patient as a function of time, said angle $\alpha$ being indicative of the combined motion of both hip and spine of the patient;
   (f) means connected to the recording means for processing the recorded positions of the skin-markers symmetrically fixed on the ilium with the recorded position of the skin-marker fixed on the sacral vertebra $S_3$ to determine the angle of rotation "h" of the hp as a function of time, said angle "h" being indicative of the hip motion of the patient;
   (g) means connected to processing means (e) and (f) for subtracting angle "h" from angle $\alpha$ to determine the actual contribution of the spine to the total flexion of the patient as a function of time, said contribution, expressed as angle "s", being indicative of the spine motion of the patient;
   (h) means connected to processing means (e) and (f) for calculating the relative variations of angles "h" and "s" versus angle $\alpha$; and
   (i) means connected to said calculating means (h) for plotting the processed variations of "h" and "s" versus $\alpha$, said variations being respectively indicative of the ranges of hip and spine motion in the sagittal plane.

3. An equipment as claimed in claim 2, wherein:
   the skin-markers (a) and (b) consists of LEDs fired at given intervals by a first computer;
   the visualization equipment (c) consists of a pair of cameras spaced apart from each other in order to tract and monitor the relative positions of the LEDs in the space while said LEDs are fired; and
   all of said recording, processing and calculating means (d) to (h) are included into an other computer.

4. An equipments as claimed in claim 3, wherein said other computer further includes:
   (j) means for measuring the lumbosacral angle $\Psi$ as a function of time when the patient is flexing, said g means comprising:
   means for mathematically reconstructing the true lumbar curve of the spine of the sagittal plane from the respective, recorded positions of the LEDs in the midline of the patient's back;

means for locating the inflexion point on the reconstructed curve; and means for tracing tangents to said inflexion point, and means for measuring the angle between said tangents, said measured angle being used as angle $\Psi$; and (k) means for processing the measured values of to calculate the relative variation of said angle $\Psi$ versus $\alpha$, said variation being indicative of the lumbar lordosis of the patient's spine and thus directly correlated with the range of spine motion, said relative variation of said angle $\Psi$ versus being plotted by said plotting means (i).

5. An equipment as claimed in claim 3, wherein said other computer further includes:

(1) means for measuring the percentage of elongation of the arc sustained by the skin-markers in the midline of the patient's back while said patient is flexing, said measuring means including:

means for mathematically reconstructing the true lumbar curve of the spine of the patient in a sagittal plane from the respective, recorded positions of the markers in the midline of the patient's back; and means for measuring the distance along the curve between the markers; and (m) means for processing the measured values of percentage arc elongation to calculate the relative variation of said elongation versus $\alpha$, said variation being indicative of the lumbar lordosis of the patient's spine and thus directly correlated into the range of spine motion, said relative variation of said elongation versus $\alpha$ being plotted by said plotting means (i).

6. An equipment as claimed in claim 3, further comprising:

(o) a set of surface electrodes for measuring the electromyographic (EMG) activities of the patient bilaterally on the latissimus dorsi below scapula, the longissimus lumboruni at vertebra $L_3$, the multifidus at $L_5$ and the hamstring semitendinosus; and (p) means for integrating said EMG signals to determine the magnitude of activity of every muscle, said integrated signals being plotted by said plotting means (i) as a function of time.

7. An equipment as claimed in claim 3, further comprising:

(q) further dot-sized skin-markers attachable bi-laterally and symmetrically onto the back, shoulders, arms above the elbows and legs below the knees and at the Achilles tendons to track with the cameras the general position of the patient while he is flexing forward.

8. An equipment as claimed in claim 3, further comprising:

(r) means for measuring the relative motion of each skin-markers fixed in the midline of the patient's spine with respect to the skin-marker immediately below; and (s) means for plotting the measured values of said relative motion during flexion and extension respectively, said plotted values being indicative of contribution of each spinal segment to the flexibility of the spine in the lumbar region.

9. A non-invasive method for the evaluation of the flexibility of the spine of a patient and, as a result of this evaluation, the detection and identification of possible mechanical injuries in the cervical portion of said spine, said method comprising the steps of:

(a) detachably fixing a string of separate, dot-sized skin-markers onto the skin of the back and neck of the patient in the mid-line of his spine from at least thoracic vertebra T-5 up to the skull;

(b) detachably fixing two other dot-sized skin-markers onto the skin of the back of the patient in a bilateral and symmetrical manner on the crests of his scapulae;

(c) detachably fixing at least two further dot-sized skin-markers onto the rear of the head of the patient in a bilateral and symmetrical manner;

(d) tracking the relative positions of all of said skin-markers on the back, neck and head of the patient with a pair of cameras spaced apart from each other in order to monitor and record the relative positions of the skin-markers in a space as the patient moves his neck;

(e) processing the so recorded positions of the skin-markers to measure the scapulae motion and evaluate its contribution to the neck motion;

(f) further processing the recorded positions of the skin-markers to measure the cervical spine motion;

(g) extracting from the measured cervical spine motion the intersegment and segmental mobilities of the cervical spine;

(h) plotting said processed and extracted data; and (i) comparing the plots with each other and with plots obtained from the group of "normal" patients to determine any discrepancy or singularity and derive from these comparisons and determination the requested information as to the flexibility of the cervical portion of the spine and the presence of a potential mechanical injury therein.

10. A non-invasive method for the evaluation of the flexibility of the spine of a patient and, as a result of this evaluation, the detection and identification of possible mechanical injuries in the lumbar portion of this spine, said method comprising the steps of:

(a) detachably fixing a string of separate, dot-sized skin-markers onto the skin of the back of the patient in the midline of his spine from at least cervical vertebra $C_7$ down to at least sacral vertebra $S_3$;

(b) detachably fixing two other dot-sized skin-markers onto the skin of the back of the patient in a bilateral and symmetrical manner on the crests of the ilium of the patient;

(c) monitoring and recording the relative positions of all of said skin-markers on the back of the patient as he flexes forward in this sagittal plane;

(d) processing the recorded positions of the skin-markers fixed in the midline of the patient's back to determine the angle of flexion $\alpha$ of the patient as a function of time, said angle $\alpha$ being indicative of the combined motion of both hip and spine of the patient;

(e) processing the recorded positions of the skin-markers symmetrically fixed on the ilium with the recorded position of the skin-marker fixed on a sacral vertebra to determine the angle of rotation "h" of the hip as a function of time, said angle "h" being indicative of the hip motion of the patient;

(f) substracting angle "h" from angle to determine the actual contribution of the spine to the total flexion of the patient as a function of time, said contribution, expressed as angle "s", being indicative of the spine motion of the patient; and (g) processing the values of angles $\alpha$, "h" and "s" to calculate the relative variations of "h" and "s"

versus α, and plotting said variations which are respectively indicative of the ranges of hip and spine motions in the sagittal plane; and (h) comparing said plots with each other and with plots obtained from a group "normal" patients to determine any discrepancy or singularity and derive from these comparison and determination the requested information as to the flexibility of the spine and the presence of a potential mechanical injury therein.

11. The method of claim 10 wherein, in steps (a) and (b), use is made of LEDs fired under computer control, as skin-markers, and wherein step (c) is carried out with a pair of cameras spaced apart from each other in order to track, monitor and record the relative positions of the LEDs in the space when said LEDs are fired.

12. The method of claim 11, wherein, in step (d) the determination of angle α is carried out by mathematically drawing an imaginary line passing through one of the uppermost LEDs in the midline of the patient's back and one the lowermost LEDs fixed on a sacral vertebra, and measuring the angle between said imaginary line and a vertical axis, said measured angle being used as angle α.

13. The method of claim 11, wherein, in step (d), the determination of angle α is carried out by using the respective, recorded position of every LED in the midline of the patient's back to mathematically draw a mean-square fit line indicative of the general angle of flexion of the patient and measuring the angle between said line and a vertical axis, said measured angle being used as angle α.

14. The method of claim 11, comprising the additional steps of:

(i) measuring the lumbo-sacral angle Ψ as a function of time while the patient is flexing, said measurement being carried out by using the respective, recorded positions of the LEDs in the midline of the patient's back to mathematically reconstruct the true lumbar curve of the spine in the sagittal plane, then locating the inflexion point on the reconstructed curve and tracing tangents to said inflexion points, and finally measuring the angle between said tangents, said measured angle being used as angle Ψ.

(j) processing the measured values of Ψ to calculate the relative variation of said angle α versus α, and plotting said variation which is indicative of the lumbar lordosis of the patient's spine and thus directly correlated with the range of spine motion; and (k) using this plot as further information to detect the presence of a potential mechanical injury in the lumbar spine of the patient.

15. The method of claim 11, comprising the additional steps of:

(1) measuring the percentage of elongation of the arc sustained by the skin markers while the patient is flexing, by using the respective, recorded positions of said markers in the midline of the patient's back to mathematically reconstruct the true lumbar curve of the spine in the sagittal plane and then measuring the distance along the curve between the markers;

(m) processing the measured values of percentage arc elongation to calculate the relative variation of said elongation versus α, and plotting said variation which is indicative of the lumbar lordosis of the patient's spine and thus directly correlated with the range of spine motion, and (n) using this plot as further information to detect the presence of a potential mechanical injury in the lumbar spine of the patient.

16. The method of claim 11, comprising the additional steps of:

(o) measuring with a set of surface electrodes the electromyographic (EMG) activities of the patient bilaterally on the latissimus dorsi below scapula, the longissimus lumboruni at vertebra $L_3$, the multifidus at $L_5$ and the hamstring semitendinosus;

(p) integrating said EMG signals to determine the magnitude of activity of every muscle;

(q) plotting said integrated signals as a function of time; and (r) comparing the plots obtained on the left and right sides of the patient to note any discrepancy, and using this information as well as the general muscle activity as reflected by all of these EMG plots as a further information to detect the presence of a potential mechanical injury in the lumbar spine of the patient.

17. The method of claim 11, comprising the additional steps of:

(s) detachably fixing further dot-sized skin-markers bilaterally and symmetrically onto the shoulders, the arms above the elbows and the legs below the knees and at the Achilles tendons; and (t) using said further skin-markers to tract the general position of the patient while he is flexing forward.

18. The method of claim 11, comprising the additional steps of:

(u) measuring the relative motion of each of the skin-markers fixed in the midline of the patient's spine with respect to the skin-marker immediately below it; and (v) plotting the measured values of said relative motions during flexion and extension, respectively, said plotted values being indicative of the contribution of each spinal segment to the flexibility of the spine in the lumbar region.

* * * * *